United States Patent
Bell et al.

(10) Patent No.: US 8,143,266 B2
(45) Date of Patent: Mar. 27, 2012

(54) ARYL HETEROCYCLIC CGRP RECEPTOR ANTAGONISTS

(75) Inventors: Ian M. Bell, Harleysville, PA (US);
Harold G. Selnick, Ambler, PA (US);
Craig A. Stump, Pottstown, PA (US)

(73) Assignee: Merck, Sharp & Dohme Corp, Rahway, NJ (US)

( * ) Notice: Subject to any disclaimer, the term of this patent is extended or adjusted under 35 U.S.C. 154(b) by 310 days.

(21) Appl. No.: 12/595,704

(22) PCT Filed: Apr. 11, 2008

(86) PCT No.: PCT/US2008/004786
§ 371 (c)(1), (2), (4) Date: Oct. 13, 2009

(87) PCT Pub. No.: WO2008/130524
PCT Pub. Date: Oct. 30, 2008

(65) Prior Publication Data
US 2010/0120809 A1    May 13, 2010

Related U.S. Application Data

(60) Provisional application No. 60/923,851, filed on Apr. 16, 2007.

(51) Int. Cl.
*A61K 31/437* (2006.01)
*C07D 221/20* (2006.01)
(52) U.S. Cl. .......... 514/278; 546/15
(58) Field of Classification Search .......... 514/278; 546/15
See application file for complete search history.

(56) References Cited

U.S. PATENT DOCUMENTS

| | | |
|---|---|---|
| 7,189,722 B2 | 3/2007 | Bell et al. |
| 7,192,954 B2 | 3/2007 | Bell et al. |
| 7,390,798 B2 | 6/2008 | Williams et al. |
| 2008/0096878 A1 | 4/2008 | Bell et al. |
| 2008/0214511 A1 | 9/2008 | Bell et al. |
| 2009/0054408 A1 | 2/2009 | Bell et al. |

FOREIGN PATENT DOCUMENTS

| | | |
|---|---|---|
| WO | 96/18616 | 6/1996 |
| WO | 2004/082605 A2 | 9/2004 |
| WO | 2006/031513 A2 | 3/2006 |
| WO | 2006/031676 A2 | 3/2006 |
| WO | 2008/020902 A1 | 2/2008 |
| WO | 2008/112159 A1 | 9/2008 |

OTHER PUBLICATIONS

International Search Report for PCT/US08/04786, 2008.

*Primary Examiner* — Kamal Saeed
*Assistant Examiner* — Kristin Bianchi
(74) *Attorney, Agent, or Firm* — Nicole M. Beeler; Gerard M. Devlin

(57) ABSTRACT

Compounds of formula I:

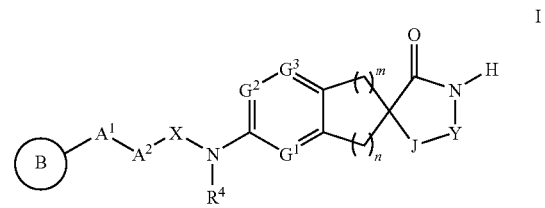

(wherein variables $A^1$, $A^2$, B, m, n, J, X, $R^4$, $G^1$, $G^2$, $G^3$ and Y are as described herein) which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

19 Claims, No Drawings

ARYL HETEROCYCLIC CGRP RECEPTOR ANTAGONISTS

CROSS-REFERENCE TO RELATED APPLICATIONS

This application claims priority under 35 U.S.C. §119(e) of U.S. provisional application Ser. No. 60/923,851, filed Apr. 16, 2007.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), salivary levels of CGRP are elevated in migraine subjects between attacks (Bellamy et al., Headache, 2006, 46, 24-33), and CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of the formula I:

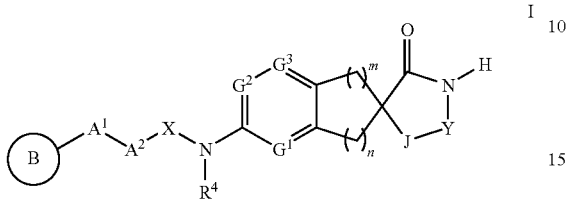

(wherein variables $A^1$, $A^2$, B, m, n, J, X, $R^4$, $G^1$, $G^2$, $G^3$ and Y are as described herein) which are antagonists of CGRP receptors and which are useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

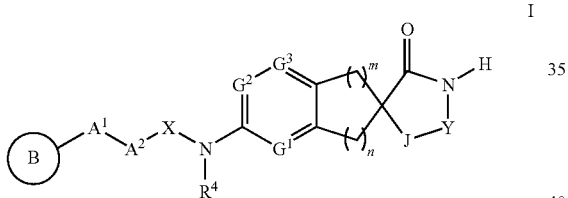

wherein:

B is a selected from the group consisting of: $C_{3-10}$cycloalkyl, phenyl, naphthyl, tetrahydronaphthyl, indanyl, biphenyl, phenanthryl, anthryl, azepanyl, azepinyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepanyl, oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiazolyl, thiazolinyl, thienofuryl, thienothienyl, thienyl and triazolyl, where B is linked to $A^1$ via a carbon atom in B, and where B is unsubstituted or substituted with 1-5 substituents, each substituent independently selected from $R^1$, $R^2$, $R^{3a}$ and $R^{3b}$, wherein $R^1$, $R^2$, $R^{3a}$ and $R^{3b}$ are each independently selected from:
(1) —$C_{1-6}$alkyl, which is unsubstituted or substituted with 1-7 substituents, each substituent independently selected from:
(a) halo,
(b) hydroxy,
(c) —O—$C_{1-6}$alkyl,
(d) —$C_{3-6}$cycloalkyl,
(e) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each substituent independently selected from: —$C_{1-6}$alkyl, —O—$C_{1-6}$alkyl, halo, hydroxy, trifluoromethyl and —$OCF_3$,
(f) —$CO_2R^9$, wherein $R^9$ is selected from: hydrogen, —$C_{5-6}$cycloalkyl, benzyl, phenyl, and —$C_{1-6}$alkyl which is unsubstituted or substituted with 1-6 fluoro,
(g) —$NR^{10}R^{11}$, wherein $R^{10}$ and $R^{11}$ are each independently selected from: hydrogen, —$C_{5-6}$cycloalkyl, benzyl, phenyl, —$COR^9$, —$SO_2R^{12}$, and —$C_{1-6}$alkyl which is unsubstituted or substituted with 1-6 fluoro,
(h) —$SO_2R^{12}$, wherein $R^{12}$ is selected from: —$C_{5-6}$cycloalkyl, benzyl, phenyl and —$C_{1-6}$alkyl which is unsubstituted or substituted with 1-6 fluoro,
(i) —$CONR^{10a}R^{11a}$, wherein $R^{10a}$ and $R^{11a}$ are each independently selected from: hydrogen, —$C_{5-6}$cycloalkyl, benzyl, phenyl and —$C_{1-6}$alkyl which is unsubstituted or substituted with 1-6 fluoro,
or wherein $R^{10a}$ and $R^{11a}$ join to form a ring selected from azetidinyl, pyrrolidinyl, piperidinyl, piperazinyl, and morpholinyl, where said ring is unsubstituted or substituted with 1-5 substituents, each substituent independently selected from: —$C_{1-6}$alkyl, —O—$C_{1-6}$alkyl, halo, hydroxyl, phenyl and benzyl,
(j) trifluoromethyl,
(k) —$OCO_2R^9$,
(l) —$(NR^{10a})CO_2R^9$,
(m) —$O(CO)NR^{10a}R^{11a}$, and
(n) —$(NR^9)(CO)NR^{10a}R^{11a}$,
(2) —$C_{3-6}$cycloalkyl, which is unsubstituted or substituted with 1-7 substituents each independently selected from:
(a) halo,
(b) hydroxy,
(c) —O—$C_{1-6}$alkyl,
(d) trifluoromethyl, and
(e) phenyl, which is unsubstituted or substituted with 1-5 substituents each independently selected from: —$C_{1-6}$alkyl, —O—$C_{1-6}$alkyl, halo, hydroxy and trifluoromethyl,
(3) phenyl or heterocycle, wherein heterocycle is selected from: pyridyl, pyrimidinyl, pyrazinyl, thienyl, pyridazinyl, pyrrolidinyl, azetidinyl, thiazolyl, isothiazolyl, oxazolyl, isoxazolyl, imidazolyl, triazolyl, tetrazolyl, azepanyl, azepinyl, benzimidazolyl, benzopyranyl, benzofuryl, benzothiazolyl, benzoxazolyl, chromanyl, furyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, quinazolinyl, 1,3-dioxolanyl, oxadiazolyl, piperidinyl and morpholinyl, where said phenyl or heterocycle is unsubstituted or substituted with 1-5 substituents each independently selected from:

(a) —$C_{1-6}$alkyl which is unsubstituted or substituted with 1-6 fluoro,
(b) halo,
(c) hydroxy,
(d) —O—$C_{1-6}$alkyl which is unsubstituted or substituted with 1-6 fluoro,
(e) —$C_{3-6}$cycloalkyl,
(f) phenyl or heterocycle, wherein heterocycle is selected from: pyridyl, pyrimidinyl, pyrazinyl, thienyl and morpholinyl, where said phenyl or heterocycle is unsubstituted or substituted with 1-5 substituents each independently selected from: —$C_{1-6}$alkyl, —O—$C_{1-6}$alkyl, halo, hydroxy and trifluoromethyl,
(g) —$CO_2R^9$,
(h) —$NR^{10}R^{11}$,
(i) —$CONR^{10}R^{11}$, and
(j) —$SO_2R^{12}$,
(4) halo,
(5) oxo,
(6) hydroxy,
(7) —O—$C_{1-6}$alkyl which is unsubstituted or substituted with 1-5 halo,
(8) —CN,
(9) —$CO_2R^9$,
(10) —$NR^{10}R^{11}$,
(11) —$SO_2R^{12}$,
(12) —$CONR^{10a}R^{11a}$,
(13) —$OCO_2R^9$,
(14) —$(NR^{10a})CO_2R^9$,
(15) —$O(CO)NR^{10a}R^{11a}$,
(16) —$(NR^9)(CO)NR^{10a}R^{11a}$,
(17) —$SO_2NR^{10a}R^{11a}$, and
(18) —$COR^{12}$;
or $R^{3a}$ and $R^{3b}$ and the atom(s) to which they are attached are join to form a ring selected from cyclobutyl, cyclopentyl, cyclohexyl, cyclopentenyl, cyclohexenyl, azetidinyl, pyrrolidinyl, piperidinyl, tetrahydrofuranyl, tetrahydropyranyl, furanyl, dihydrofuranyl, dihydropyranyl and piperazinyl, where said ring is unsubstituted or substituted with 1-5 substituents each independently selected from:
(a) —$C_{1-6}$alkyl, which is unsubstituted or substituted with 1-3 substituents each independently selected from:
(i) halo,
(ii) hydroxy,
(iii) —O—$C_{1-6}$alkyl
(iv) —$C_{3-6}$cycloalkyl,
(v) phenyl or heterocycle, wherein heterocycle is selected from: pyridyl, pyrimidinyl, pyrazinyl, pyridazinyl, piperidinyl, piperazinyl, pyrrolidinyl, thienyl, and morpholinyl, where said phenyl or heterocycle is unsubstituted or substituted with 1-5 substituents each independently selected from: —$C_{1-6}$alkyl, —O—$C_{1-6}$alkyl, halo, hydroxy, trifluoromethyl and —$OCF_3$,
(vi) —$CO_2R^9$,
(vii) —$NR^{10}R^{11}$,
(viii) —$SO_2R^{12}$,
(ix) —$CONR^{10a}R^{11a}$, and
(x) —$(NR^{10a})CO_2R^9$,
(b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, where said phenyl or heterocycle is unsubstituted or substituted with 1-3 substituents each independently selected from: halo, hydroxy, —$C_{3-6}$cycloalkyl, —$C_{1-6}$alkyl which is unsubstituted or substituted with 1-6 fluoro and —O—$C_{1-6}$alkyl which is unsubstituted or substituted with 1-6 fluoro,
(c) halo,
(d) —$SO_2R^{12}$,
(e) hydroxy,
(f) —O—$C_{1-6}$alkyl which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$, and
(n) —$(NR^9)(CO)NR^{10a}R^{11a}$;
$A^1$ and $A^2$ are each independently selected from:
(1) a bond,
(2) —$CR^{13}R^{14}$—, wherein $R^{13}$ and $R^{14}$ are independently selected from: hydrogen, hydroxyl and $C_{1-6}$ alkyl which is unsubstituted or substituted with 1-6 fluoro,
(3) —$NR^{10}$—,
(4) —$CR^{13}R^{14}$—$NR^{10}$—,
(5) —$CR^{13}R^{14}$—$CH_2$—,
(6) —$CH_2$—$CR^{13}R^{14}$—,
(7) —O—$CR^{13}R^{14}$—,
(8) —$CR^{13}R^{14}$—O—, and
(9) —C≡C—,
(10) —$C(R^{13})$=$C(R^{14})$—, and
(11) —C(=O)—,
or wherein one of $A^1$ and $A^2$ is absent;
$G^1$, $G^2$ and $G^3$ are each independently selected from:
(1) —$C(R^5)$=,
(2) —N=, and
(3) —$(N^+$—$O^-)$=,
wherein no more than two of $G^1$, $G^2$ and $G^3$ are selected to be —$C(R^5)$=;
or wherein $G^1$ is selected from:
(1) —$C(R^5)$=,
(2) —N=, and
(3) —$(N^+$—$O^-)$=,
and -$G^2$=$G^3$- taken together are selected from:
(1) —S—,
(2) —O—,
(3) —$N(R^{10})$—;
J is selected from:
(1) =$C(R^{6a})$—,
(2) —$CR^{13}R^{14}$—,
(3) —C(=O)—, and
(4) —$N(R^{15})$—;
Y is selected from:
(1) =$C(R^{6b})$—,
(2) —$CR^{13}R^{14}$—,
(3) —C(=O)—,
(4) —$SO_2$—,
(5) =N—, and
(6) —$N(R^{6b})$—;
X is —CO— or —$SO_2$—;
$R^4$ is selected from: hydrogen, $C_{5-6}$ cycloalkyl, benzyl, phenyl and $C_{1-6}$ alkyl which is unsubstituted or substituted with 1-6 fluoro;
$R^5$ is selected from: hydrogen, $C_{1-6}$ alkyl, —O—$C_{1-6}$alkyl, —$OCF_3$, trifluoromethyl, halo, hydroxy and —CN;
$R^{6a}$ and $R^{6b}$ are each independently selected from:
(1) hydrogen;
(2) —$C_{1-4}$alkyl, which is unsubstituted or substituted with 1-5 substituents independently selected from:

(a) halo,
(b) —O—$C_{1-6}$ alkyl,
(c) —$C_{3-6}$cycloalkyl,
(d) phenyl or heterocycle, wherein heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, and morpholinyl, and wherein said phenyl or heterocycle is unsubstituted or substituted with 1-3 substituents independently selected from: —$C_{1-6}$alkyl, —O—$C_{1-6}$alkyl, halo, hydroxy, trifluoromethyl and —$OCF_3$,
(3) phenyl or heterocycle, wherein heterocycle is selected from: pyridyl, pyrimidinyl, pyrazinyl, thienyl, pyrrolidinyl, azetidinyl, thiazolyl, oxazolyl, imidazolyl, triazolyl, tetrahydrofuryl, piperidinyl, and morpholinyl, which is unsubstituted or substituted with 1-3 substituents independently selected from:
    (a) —$C_{1-4}$alkyl, which is unsubstituted or substituted with 1-5 fluoro,
    (b) halo,
    (c) hydroxy,
    (d) —O—$C_{1-4}$alkyl, which is unsubstituted or substituted with 1-5 fluoro,
    (e) —$C_{3-6}$cycloalkyl, and
    (f) phenyl,
(4) halo,
(5) hydroxy,
(6) —O—$C_{1-6}$alkyl, which is unsubstituted or substituted with 1-5 halo,
(7) —CN,
(8) —$CO_2R^9$,
(9) —$NR^{10}R^{11}$, and
(10) —$CONR^{10a}R^{11a}$;
or $R^{6a}$ and $R^{6b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl, and dihydrothiopyranyl, where said ring is unsubstituted or substituted with 1-5 substituents each independently selected from:
    (a) —$C_{1-6}$alkyl, which is unsubstituted or substituted with 1-3 substituents each independently selected from:
        (i) halo,
        (ii) hydroxy,
        (iii) —O—$C_{1-6}$alkyl,
        (iv) —$C_{3-6}$cycloalkyl,
        (v) phenyl or heterocycle, wherein heterocycle is selected from: pyridyl, pyrimidinyl, pyrazinyl, pyridazinyl, piperidinyl, piperazinyl, pyrrolidinyl, thienyl, and morpholinyl, which is unsubstituted or substituted with 1-5 substituents each independently selected from: —$C_{1-6}$alkyl, —O—$C_{1-6}$alkyl, halo, hydroxy, trifluoromethyl, and —$OCF_3$,
        (vi) —$CO_2R^9$,
        (vii) —$NR^{10}R^{11}$,
        (viii) —$SO_2R^{12}$,
        (ix) —$CONR^{10a}R^{11a}$, and
        (x) —$(NR^{10a})CO_2R^9$,
    (b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, where said phenyl or heterocycle is unsubstituted or substituted with 1-3 substituents each independently selected from: —$C_{3-6}$cycloalkyl, halo, hydroxy, —O—$C_{1-6}$alkyl which is unsubstituted or substituted with 1-6 fluoro, and —$C_{1-6}$alkyl which is unsubstituted or substituted with 1-6 fluoro,
    (c) halo,
    (d) —$SO_2R^{12}$,
    (e) hydroxy,
    (f) —O—$C_{1-6}$alkyl which is unsubstituted or substituted with 1-5 halo,
    (g) —CN,
    (h) —$COR^{12}$,
    (i) —$NR^{10}R^{11}$,
    (j) —$CONR^{10a}R^{11a}$,
    (k) —$CO_2R^9$,
    (l) —$(NR^{10a})CO_2R^9$,
    (m) —$O(CO)NR^{10a}R^{11a}$,
    (n) —$(NR^9)(CO)NR^{10a}R^{11a}$, and
    (o) oxo;
$R^{15}$ is selected from:
    (1) hydrogen,
    (2) —$C_{1-6}$alkyl or —$C_{3-6}$cycloalkyl which are unsubstituted or substituted with 1-7 substituents where the substituents are independently selected from:
        (a) halo,
        (b) hydroxy,
        (c) —O—$C_{1-6}$alkyl,
        (d) —$C_{3-6}$cycloalkyl,
        (e) phenyl, which is unsubstituted or substituted with 1-5 substituents where the substituents are independently selected from:
            (i) —$C_{1-6}$alkyl,
            (ii) —O—$C_{1-6}$alkyl,
            (iii) halo,
            (iv) hydroxy, and
            (v) trifluoromethyl,
        (f) —$CO_2R^9$,
        (g) —$NR^{10}R^{11}$,
        (h) —$CONR^{10}R^{11}$,
        (i) —$SO_2R^{12}$, and
        (j) trifluoromethyl, and
    (3) phenyl or heterocycle, wherein heterocycle is selected from: pyridyl, pyrimidinyl, pyrazinyl, thienyl, and morpholinyl, which is unsubstituted or substituted with 1-5 substituents where the substituents are independently selected from:
        (a) —$C_{1-6}$alkyl,
        (b) —O—$C_{1-6}$alkyl,
        (c) halo,
        (d) hydroxy, and
        (e) trifluoromethyl;
m is 1 or 2;
n is 1 or 2;
and pharmaceutically acceptable salts thereof and individual enantiomers and diastereomers thereof.

An embodiment of the present invention includes compounds of the formula Ia:

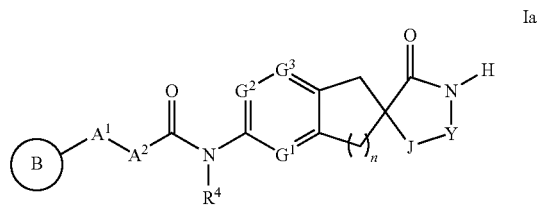

Ia wherein $A^1$, $A^2$, $G^1$, $G^2$, $G^3$, B, J, Y, $R^4$, and n are defined herein; and pharmaceutically acceptable salts thereof and individual enantiomers and diastereomers thereof.

Another embodiment of the present invention includes compounds of the formula Ib:

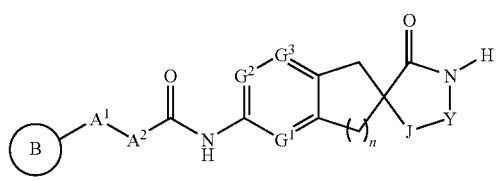

Ib wherein $A^1$, $A^2$, $G^1$, $G^2$, $G^3$, B, J, Y, and n are defined herein; and pharmaceutically acceptable salts thereof and individual enantiomers and diastereomers thereof.

Another embodiment of the present invention includes compounds of the formula Ic:

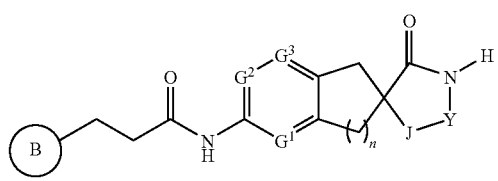

Ic wherein $G^1$, $G^2$, $G^3$, B, J, Y, and n are defined herein; and pharmaceutically acceptable salts thereof and individual enantiomers and diastereomers thereof.

Another embodiment of the present invention includes compounds of the formula Id:

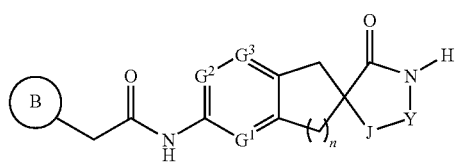

Id wherein $G^1$, $G^2$, $G^3$, B, J, Y, and n are defined herein; and pharmaceutically acceptable salts thereof and individual enantiomers and diastereomers thereof.

Another embodiment of the present invention includes compounds of the formula Ie:

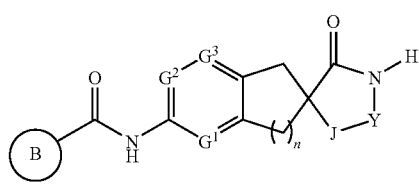

Ie wherein $G^1$, $G^2$, $G^3$, B, J, Y, and n are defined herein; and pharmaceutically acceptable salts thereof and individual enantiomers and diastereomers thereof.

Another embodiment of the present invention includes compounds of the formula If:

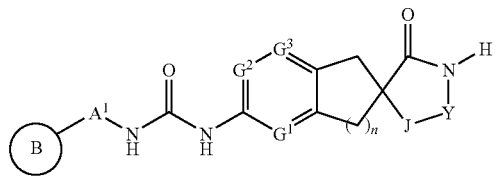

If wherein $A^1$, $G^1$, $G^2$, $G^3$, B, J, Y, and n are defined herein; and pharmaceutically acceptable salts thereof and individual enantiomers and diastereomers thereof.

Another embodiment of the present invention includes compounds of the formula Ig:

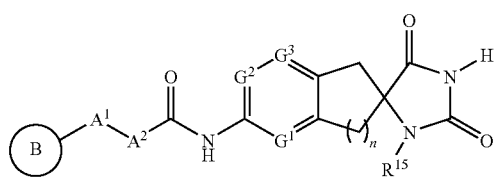

Ig wherein $A^1$, $A^2$, $G^1$, $G^2$, $G^3$, B, $R^{15}$, and n are defined herein; and pharmaceutically acceptable salts thereof and individual enantiomers and diastereomers thereof.

Another embodiment of the present invention includes compounds of the formula Ih:

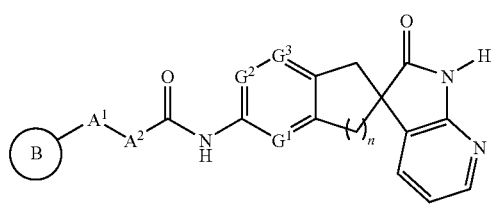

Ih wherein $A^1$, $A^2$, $G^1$, $G^2$, $G^3$, B, and n are defined herein; and pharmaceutically acceptable salts thereof and individual enantiomers and diastereomers thereof.

In an embodiment of the present invention B is selected from: $C_{3-10}$cycloalkyl, phenyl, napthyl, tetrahydronaphthyl, indanyl, indolyl, indolinyl, isoindolinyl, isoquinolinyl, morpholinyl, naphthyridinyl, piperidyl, piperazinyl, pyrazinyl, pyridazinyl, pyridinyl, pyridyl, pyrimidinyl, pyrimidyl, pyrrolidinyl, quinazolinyl, quinolinyl, quinoxalinyl, thiazolyl and thienyl, unsubstituted or substituted with 1-5 substituents each independently selected from $R^1$, $R^2$, $R^{3a}$ and $R^{3b}$, where $R^1$, $R^2$, $R^{3a}$, and $R^{3b}$ are defined herein.

In an embodiment of the present invention B is phenyl.
In an embodiment of the present invention B is thienyl.
In an embodiment of the present invention B is pyridyl.
In an embodiment of the present invention B is pyridinyl.
In an embodiment of the present invention B is quinolinyl.
In an embodiment of the present invention B is quinoxalinyl.
In an embodiment of the present invention B is naphthyl.
In an embodiment of the present invention B is norbornyl.
In an embodiment of the present invention B is cyclohexyl.
In an embodiment of the present invention B is cyclopentyl.

In an embodiment of the present invention B is cyclopropyl.

In an embodiment of the present invention B is thiazolyl.

In an embodiment of the present invention B is indanyl.

In an embodiment of the present invention B is indolinyl.

In an embodiment of the present invention B is tetrahydroquinolinyl.

In an embodiment of the present invention $R^1$, $R^2$, $R^{3a}$ and $R^{3b}$ are independently selected from:
(1) $C_{1-6}$ alkyl, which is unsubstituted or substituted with 1-5 fluoro,
(2) $C_{3-6}$ cycloalkyl,
(3) —O—$C_{1-6}$alkyl,
(4) —$OCF_3$,
(5) trifluoromethyl,
(6) halo,
(7) oxo
(8) —CN,
(9) —$COR^{12}$,
(10) —$CO_2R^{12}$,
(11) —$CONR^{10a}R^{11a}$,
(12) phenyl, which is unsubstituted or substituted with 1-5 substituents each independently selected from: $C_{1-6}$alkyl, —O—$C_{1-6}$alkyl, halo, —OH and —$CF_3$,
(13) heterocycle selected from: pyridyl, pyrimidinyl, pyrazinyl, thienyl, pyrrolidinyl, piperidinyl or morpholinyl, which is unsubstituted or substituted with 1-5 substituents each independently selected from: $C_{1-6}$alkyl, —O—$C_{1-6}$alkyl, halo, —OH and —$CF_3$.

In an embodiment of the present invention $A^1$ is a bond.

In an embodiment of the present invention $A^1$ is —$CH_2$—.

In an embodiment of the present invention $A^1$ is —$OCH_2$—.

In an embodiment of the present invention $A^1$ is —C≡C—.

In an embodiment of the present invention $A^1$ is —$CH_2$—$NR^{10}$—, where $R^{10}$ is defined herein.

In an embodiment of the present invention $A^1$ is —$NR^{10}$—.

In an embodiment of the present invention $A^1$ is —C(H)═C(H)—.

In an embodiment of the present invention $A^2$ is a bond.

In an embodiment of the present invention $A^2$ is —$CH_2$—.

In an embodiment of the present invention $A^2$ is —NH—.

In an embodiment of the present invention $A^2$ is —$CH_2$—NH—.

In an embodiment of the present invention J is selected from: ═C($R^{6a}$)—; —$CH_2$—; and —N($R^{15}$)—; wherein $R^{6a}$ and $R^{15}$ are defined herein. In another embodiment of the present invention J is —$CH_2$—. In another embodiment of the present invention J is —N($R^{15}$)—; wherein $R^{15}$ is defined herein. In yet another embodiment of the present invention J is ═C($R^{6a}$)—; wherein $R^{6a}$ is defined herein.

In an embodiment of the present invention Y is selected from: ═C($R^{6b}$)—; —$CH_2$—; and —C(═O)—; wherein $R^{6b}$ is defined herein. In another embodiment of the present invention Y is —$CH_2$—. In another embodiment of the present invention Y is —C(═O)—. In yet another embodiment of the present invention Y is ═C($R^{6b}$)— wherein $R^{6b}$ is defined herein.

In an embodiment of the present invention X is —CO—.

In an embodiment of the present invention X is —$SO_2$—.

In an embodiment of the present invention $R^4$ is hydrogen.

In an embodiment of the present invention $R^5$ is selected from hydrogen, $C_{1-6}$alkyl and halo.

In an embodiment of the present invention $R^5$ is selected from hydrogen and halo.

In an embodiment of the present invention $R^5$ is hydrogen.

In an embodiment of the present invention $R^{6a}$ and $R^{6b}$ are each in dependently selected from:
(1) hydrogen;
(2) —$C_{1-4}$alkyl, which is unsubstituted or substituted with 1-3 substituents each independently selected from: halo, —O—$C_{1-6}$alkyl, —$C_{3-6}$cycloalkyl and phenyl,
(3) phenyl or heterocycle, wherein heterocycle is selected from: pyridyl, pyrimidinyl, pyrazinyl, thiazolyl, oxazolyl, tetrahydrofuryl, piperidinyl, and morpholinyl, where said phenyl or heterocycle is unsubstituted or substituted with 1-3 substituents each independently selected from:
(a) —$C_{1-4}$alkyl, which is unsubstituted or substituted with 1-3 fluoro,
(b) halo,
(c) hydroxy, and
(d) —O—$C_{1-4}$alkyl, which is unsubstituted or substituted with 1-3 fluoro,
(4) halo,
(5) —$NR^{10}R^{11}$,
(6) hydroxy,
(7) —O—$C_{1-4}$alkyl, which is unsubstituted or substituted with 1-3 halo.

In an embodiment of the present invention $R^{6a}$ and $R^{6b}$ are in dependently selected from:
(1) hydrogen;
(2) —$C_{1-4}$alkyl, which is unsubstituted or substituted with 1-3 fluoro, and
(3) phenyl or heterocycle, wherein heterocycle is selected from: pyridyl, pyrimidinyl, pyrazinyl, thiazolyl, oxazolyl, tetrahydrofuryl, piperidinyl, and morpholinyl.

In an embodiment of the present invention $R^{6a}$ and $R^{6b}$ and the atom(s) to which they are attached join to form a ring selected from phenyl, pyridyl, pyrimidinyl, pyrazinyl, pyridazinyl, thiazolyl, oxazolyl, imidazolyl and thienyl, where said ring is unsubstituted or substituted with 1-3 substituents each independently selected from:
(a) —$C_{1-4}$alkyl, which is unsubstituted or substituted with 1-3 substituents where the substituents are each independently selected from: halo, —O—$C_{1-6}$alkyl, —$CO_2R^9$, —$NR^{10}R^{11}$ and —$CONR^{10a}R^{11a}$,
(b) phenyl or heterocycle, wherein heterocycle is selected from: pyridyl, pyrimidinyl, pyrazinyl, pyrrolidinyl, azetidinyl, piperidinyl and morpholinyl, where said phenyl or heterocycle is unsubstituted or substituted with 1-3 substituents each independently selected from: halo, hydroxy, —$C_{1-4}$alkyl which is unsubstituted or substituted with 1-5 fluoro and —O—$C_{1-4}$alkyl which is unsubstituted or substituted with 1-3 fluoro,
(c) halo,
(d) hydroxy,
(e) —O—$C_{1-6}$alkyl, which is unsubstituted or substituted with 1-5 halo,
(f) —CN,
(g) —$NR^{10}R^{11}$,
(h) —$CONR^{10a}R^{11a}$, and
(i) oxo.

In an embodiment of the present invention $R^{6a}$ and $R^{6b}$ and the atom(s) to which they are attached join to form a ring selected from phenyl, pyridyl, and pyrimidinyl, where said ring is unsubstituted or substituted with 1-3 substituents each independently selected from: halo, hydroxy, —O—$C_{1-4}$alkyl and —$C_{1-4}$alkyl unsubstituted or substituted with 1-3 fluoro.

In an embodiment of the present invention $R^{6a}$ and $R^{6b}$ and the atom(s) to which they are attached join to form a ring selected from pyridyl, and pyrimidinyl.

In an embodiment of the present invention $G^1$, $G^2$ and $G^3$ are each independently selected from: —C($R^5$)= and —N=; wherein no more than two of $G^1$, $G^2$ and $G^3$ are selected to be —C($R^5$)=; and $R^5$ is defined herein.

In another embodiment of the present invention $G^1$ is selected from: —C($R^5$)= and —N=; and -$G^2$=$G^3$- taken together are selected from: —S— and —N($R^{10}$)—; wherein $R^5$ and $R^{10}$ are defined herein.

In yet another embodiment of the present invention one of $G^1$, $G^2$ and $G^3$ is —N= and the remaining two of $G^1$, $G^2$ and $G^3$ are —C(H)=.

In an embodiment of the present invention $R^{15}$ is selected from:
(1) hydrogen,
(2) —$C_{1-4}$alkyl which is unsubstituted or substituted with 1-3 substituents each independently selected from: halo and phenyl.

In an embodiment of the present invention $R^{15}$ is hydrogen or methyl.

In an embodiment of the present invention $R^{15}$ is methyl.
In an embodiment of the present invention m is 1.
In an embodiment of the present invention n is 1.
In an embodiment of the present invention n is 2.

It is to be understood that where one or more of the above recited structures or substructures recite multiple substituents having the same designation each such variable may be the same or different from each similarly designated variable. For example, $R^9$ is recited multiple times in certain configurations of formula I, and each instance of $R^9$ in formula I may independently be any of the substructures defined under $R^9$. The invention is not limited to structures and substructures wherein each $R^9$ must be the same for a given structural configuration. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The present invention includes compounds of formula I wherein on or more hydrogen atoms are replaced by deuterium.

Tautomers of compounds defined in Formula I are also included within the scope of the present invention. For example, compounds including carbonyl —$CH_2C(O)$— groups (keto forms) may undergo tautomerism to form hydroxyl —CH=C(OH)— groups (enol forms). Both keto and enol forms are included within the scope of the present invention.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^{10}$ and $R^{11}$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no carbon-to-carbon double or triple bonds. Thus $C_{1-6}$alkyl is defined to identify the group as having 1, 2, 3, 4, 5 or 6 carbons in a linear or branched arrangement, such that $C_{1-6}$alkyl specifically includes, but is not limited to, methyl, ethyl, n-propyl, iso-propyl, n-butyl, iso-butyl, tert-butyl, pentyl and hexyl. "Cycloalkyl" is an alkyl, part or all of which which forms a ring of three or more atoms. $C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_{2-6}$alkynyl is defined to identify the group as having 2, 3, 4, 5 or 6 carbons in a linear or branched arrangement, such that $C_{2-6}$alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "$(F)_p C_{1-3}$ alkyl" this means that when there is one carbon, there are up to 2(1)+1=3 fluorines. When there are two carbons, there are up to 2(2)+1=5 fluorines, and when there are three carbons there are up to 2(3)+1=7 fluorines.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 µg) were incubated in 1 mL of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 µL) was added and the radioactivity was counted on a Topcount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 µg/mL streptomycin, and maintained at 37° C. and 95% humidity. Cells were subcultured by treatment with 0.25% trypsin with 0.1% EDTA in HBSS. Stable cell line generation was accomplished by co-transfecting 10 µg of DNA with 30 µg Lipofectamine 2000 (Invitrogen) in 75 cm$^2$ flasks. CL receptor and RAMP1 expression constructs were co-transfected in equal amounts. Twenty-four hours after transfection the cells were diluted and selective medium (growth medium+300 µg/mL hygromycin and 1 µg/mL puromycin) was added the following day. A clonal cell line was generated by single cell deposition utilizing a FACS Vantage SE (Becton Dickinson). Growth medium was adjusted to 150 µg/mL hygromycin and 0.5 µg/mL puromycin for cell propagation.

RECOMBINANT RECEPTOR BINDING ASSAY: Cells expressing recombinant human CL receptor/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 20 µg of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4 and 5 mM MgCl$_2$). Scintillation fluid was added and the plates were counted on a Topcount (Packard). Non-specific binding was determined and the data analysis was carried out with the apparent dissociation constant (K$_i$) determined by using a non-linear least squares fitting the bound CPM data to the equation below:

$$Y_{obsd} = \frac{Y_{min} + (Y_{max} - Y_{min})(100 - \% I_{max}/100)}{1 + ([\text{Drug}]/K_i(1 + [\text{Radiolabel}]/K_d)^{nH}}$$

$$(Y_{max} - Y_{min})(\% I_{max} - \%I_{min}/100) +$$

Where Y is observed CPM bound, Y$_{max}$ is total bound counts, Y$_{min}$ is non specific bound counts, (Y$_{max}$−Y$_{min}$) is specific bound counts, % I$_{max}$ is the maximum percent inhibition, % I min is the minimum percent inhibition, radiolabel is the probe, and the K$_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; GE Healthcare). Dose response curves were plotted and IC$_{50}$ values determined from a 4-parameter logistic fit as defined by the equation y=((a−d)/(1+(x/c)$^b$)+d, where y=response, x=dose, a=max response, d=min response, c=inflection point and b=slope.

In particular, the compounds of the following examples had activity as antagonists of the CGRP receptor in the aforementioned assays, generally with a K$_i$ or IC$_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine $A^1$ receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin $5HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin H antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-$HT_1$ agonist, especially a 5-$HT_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of some heterocyclic amine intermediates may be conducted as described in Schemes 1-4. The methodology shown in these schemes is not limited to the azaoxindoles shown but may be applied to a variety of heterocyclic systems to give the corresponding Spiro compounds. Related intermediates bearing a variety of substituents may be prepared by employing appropriately substituted starting materials or by derivatization of any intermediates and/or final products as desired by methods known in the art.

Scheme 1 shows methodology for synthesis of the key azaoxindole intermediate 4. 7-Azaindole (1) may be protected with a variety of protecting groups, such as the 2-(trimethylsilyl)ethoxymethyl group shown in Scheme 1. Following the method of Marfat and Carter [(1987) *Tetrahedron Lett.* 28, 4027], treatment of 2 with pyridine hydrobromide perbromide provides the dibromoazaoxindole 3, which may be reduced to the corresponding azaoxindole 4 by reaction with zinc.

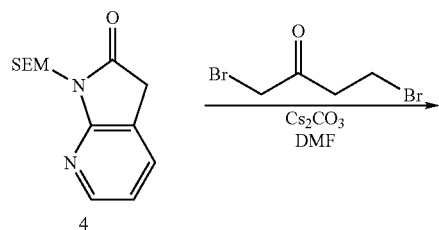

Scheme 2 illustrates a route to the 3-aminopyridine 9. Bis-alkylation of the azaoxindole 4 with 1,4-dibromobutan-2-one [de Meijere et al. (2001) *Eur. J. Org. Chem.* 3789] provides the cyclopentanone 5. Condensation of ketone 5 with ammonia and 1-methyl-3,5-dinitropyridin-2(1H)-one [Tohda et al. (1990) *Bull. Chem. Soc. Japan* 63, 2820] in refluxing methanol leads to the 3-nitropyridine derivative 6. Catalytic hydrogenation may be used to provide the corresponding amine 8. Standard deprotection of 8 using sequential acid and base treatments affords the 3-aminopyridine intermediate 9.

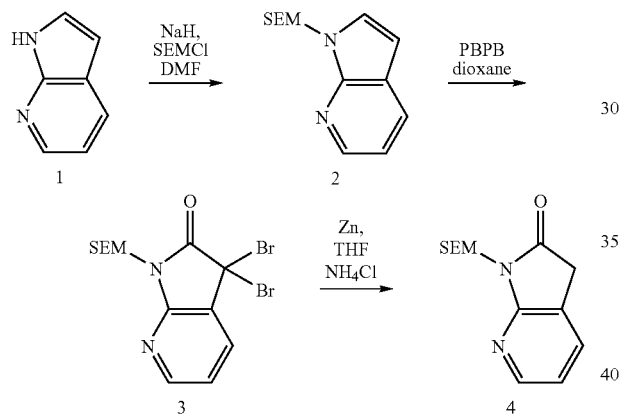

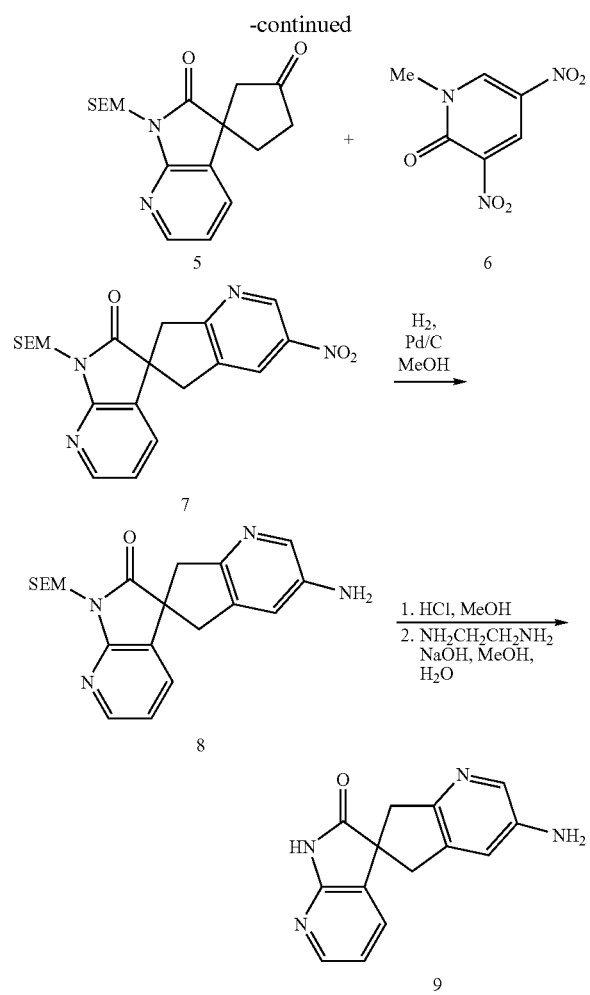

A representative synthesis of an isomer of compound 9, the 2-aminopyridine 15, is shown in Scheme 3. The known pyridine diester 10 [Hashimoto et al. (1997) *Heterocycles* 46, 581] may be reduced to the corresponding diol 11 with lithium borohydride. This diol can be converted to the dibromide 12 by reaction with phosphorus tribromide in THF. The previously described azaoxindole [Marfat & Carter (1987) *Tetrahedron Lett.* 28, 4027] may be reacted with dibromide 12 using lithium hydroxide in aqueous THF to afford the spiroazaoxindole 13. A variety of other bases and solvents may be employed in this alkylation reaction, and use of a different alkylating agent than the dibromide shown here can lead to other products. Treatment of compound 13 with aqueous NaOH at reflux effects hydrolysis of the nitrile, affording the carboxylate salt 14. This carboxylic acid salt may be subjected to known Curtius rearrangement conditions to provide, after deprotection, aminopyridine 15.

SCHEME 3

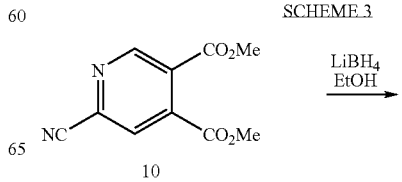

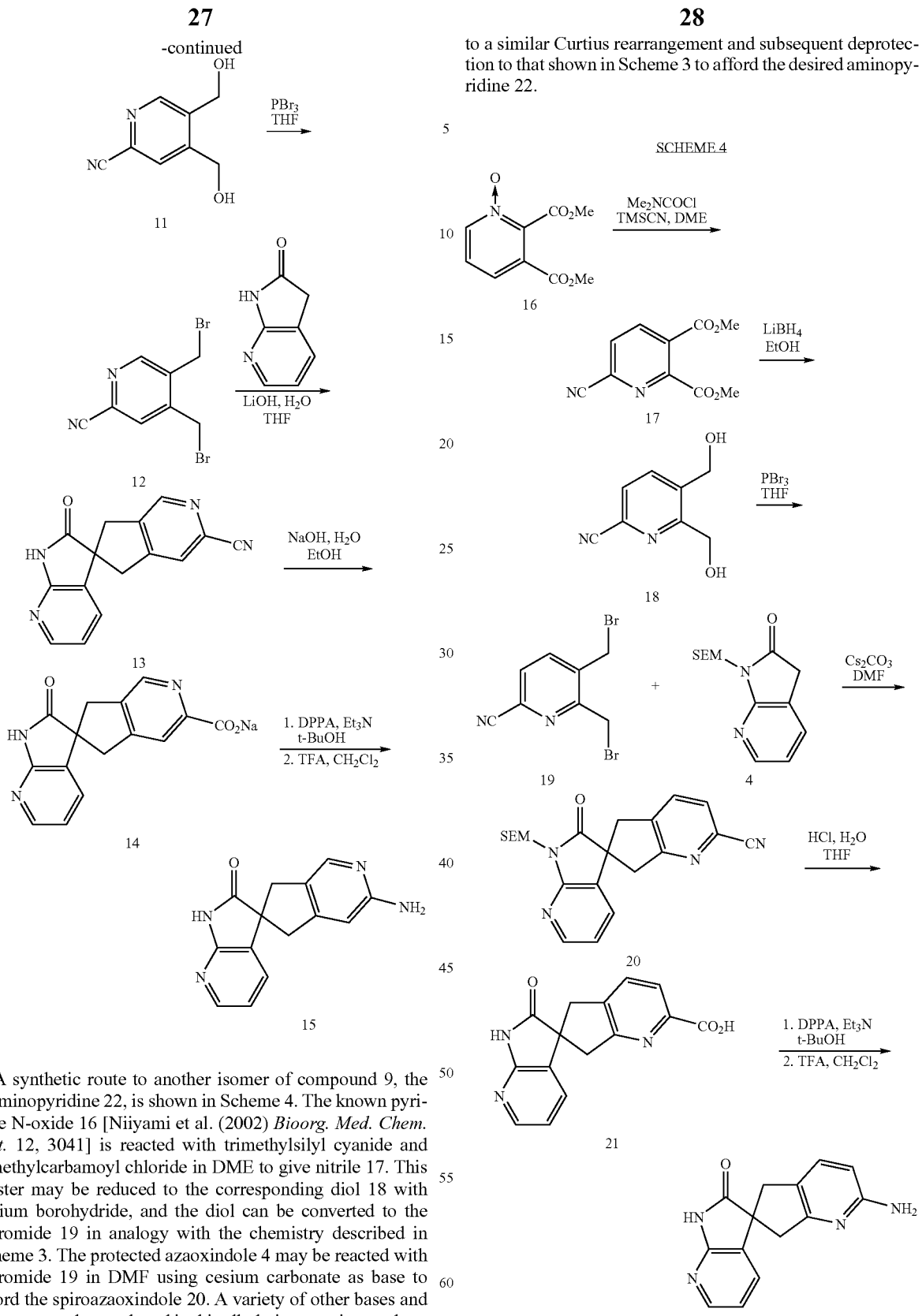

A synthetic route to another isomer of compound 9, the 2-aminopyridine 22, is shown in Scheme 4. The known pyridine N-oxide 16 [Niiyami et al. (2002) *Bioorg. Med. Chem. Lett.* 12, 3041] is reacted with trimethylsilyl cyanide and dimethylcarbamoyl chloride in DME to give nitrile 17. This diester may be reduced to the corresponding diol 18 with lithium borohydride, and the diol can be converted to the dibromide 19 in analogy with the chemistry described in Scheme 3. The protected azaoxindole 4 may be reacted with dibromide 19 in DMF using cesium carbonate as base to afford the spiroazaoxindole 20. A variety of other bases and solvents may be employed in this alkylation reaction, and use of a different alkylating agent than the dibromide shown here can lead to other products. Treatment of compound 20 with aqueous HCl at reflux effects simultaneous hydrolysis of the nitrile and deprotection of the azaoxindole, affording the key acid intermediate 21. This carboxylic acid may be subjected to a similar Curtius rearrangement and subsequent deprotection to that shown in Scheme 3 to afford the desired aminopyridine 22.

Spiroazaoxindole intermediates, such as those illustrated in these schemes (vide supra), may be resolved to give pure enantiomers using techniques familiar to those skilled in the art. For example, chromatography of the suitable intermediates on a chiral column can be used to provide the individual stereoisomers. Resolution may also be effected by other methodologies, such as fractional crystallization of diastereomeric salts, and it may be carried out on other synthetic intermediates or on the final products. Alternatively, an asymmetric synthesis of a key intermediate could be used to provide an enantiomerically enriched final product.

Amine intermediates, such as those described in Schemes 2-4, may be further elaborated by techniques familiar to one skilled in the art to provide a wide variety of final products, for example amides, ureas, and sulfonamides, as shown in Scheme 5.

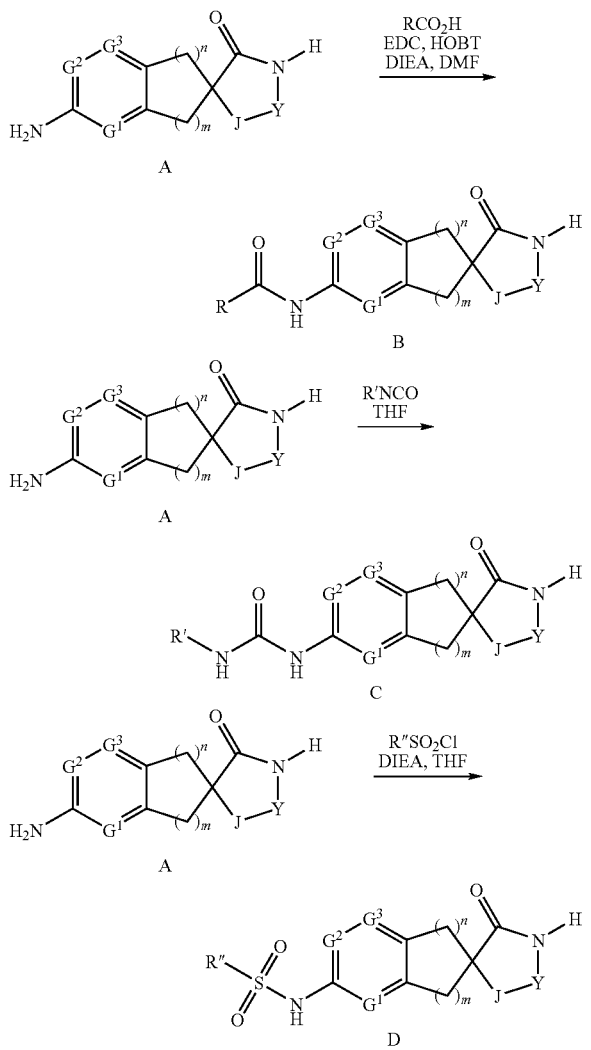

Thus, coupling of amine A with a carboxylic acid, $RCO_2H$, can be used to give amide B. Other standard coupling conditions may be employed in the synthesis of such amides, such as use of an alternative coupling reagent like PyBOP, PyCLU, or HATU, or activation of the carboxylic acid as an acid anhydride or acid chloride. Reaction of aniline A with either an isocyanate or sulfonyl chloride may be used to provide the corresponding urea (C) or sulfonamide (D) as shown in Scheme 3. Urea C may also be synthesized from aniline A and an appropriate amine ($R'NH_2$) by use of phosgene, 1,1'-carbonyldiimidazole, 4-nitrophenyl chloroformate, or a similar reagent.

Most of the acids ($RCO_2H$), isocyanates (R'NCO), and sulfonyl chlorides ($R''SO_2Cl$) used to make the compounds of the present invention are readily available. They may be obtained from commercial sources or synthesized by methodology familiar to those skilled in the art and as described in the chemical literature.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

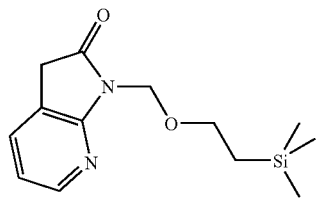

1-{[2-(Trimethylsilyl)ethoxy]methyl}-1,3-dihydro-2H-pyrrolo[2,3-b]pyridin-2-one

Step A. 1-{[2-(Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with water (500 mL) and the mixture was extracted with $CH_2Cl_2$ (5×300 mL). The combined organic layers were washed with saturated brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.1735 mol) in dioxane (300 mL) was added dropwise over 30 min to a suspension of pyridine hydrobromide perbromide (277 g, 0.8677 mol) in dioxane (300 mL). The reaction was stirred at ambient temperature using an overhead mechanical stirrer to produce two layers. After 60 min, the reaction was quenched with water (300 mL) and extracted with EtOAc (500 mL). The aqueous layer was extracted further with EtOAc (2×300 mL) and the combined organic layers were washed with $H_2O$ (4×300 mL; the final wash was pH 5-6), then brine (300 mL), dried over $MgSO_4$, filtered and concentrated in vacuo. The crude product was immediately dissolved in CH$_2$Cl$_2$ and the solution filtered through a plug of silica, eluting with CH$_2$Cl$_2$ until the dark red color had completely eluted from the plug. The filtrate was washed with saturated aqueous NaHCO$_3$ (400 mL), then brine (400 mL), dried over MgSO$_4$ filtered, and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one (65 g, 0.154 mol) in THF (880 mL) and saturated aqueous NH$_4$Cl (220 mL). After 3 h, the reaction mixture was filtered and concentrated in vacuo. The residue was partitioned between EtOAc and H$_2$O which resulted in the formation of a white precipitate. Both layers were filtered through a Celite pad and the layers were separated. The aqueous layer was washed with EtOAc (2×500 mL) and the combined organic layers were washed with H$_2$O, dried over MgSO$_4$, filtered, and concentrated under reduced pressure. The crude product was purified by silica gel chromatography, eluting with CH$_2$Cl$_2$:EtOAc—90:10, to give the title compound. MS: m/z=265 (M+1).

INTERMEDIATE 2

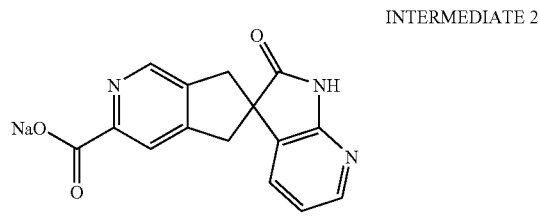

(±)-Sodium 2'-oxo-1',2',5,7-tetrahydrospiro[cyclopenta[c]pyridine-6,3'-pyrrolo[2,3-b]pyridine]-3-carboxylate Step A.
4,5-Bis(hydroxymethyl)pyridine-2-carbonitrile To a solution of dimethyl 6-cyanopyridine-3,4-dicarboxylate (2.00 g, 9.08 mmol) [Hashimoto et al. (1997) *Heterocycles* 46, 581] in EtOH (50 mL) was added lithium borohydride (4.54 mL of a 2 M solution in THF, 9.08 mmol) dropwise. The reaction mixture was stirred at ambient temperature for 3 h, and then cooled to 0° C. Saturated aqueous NaHCO$_3$ (20 mL) was added slowly and the quenched mixture was extracted with EtOAc (9×100 mL). The combined organic extracts were dried over Na$_2$SO$_4$, filtered, and concentrated in vacuo. The crude product was purified by silica gel chromatography, eluting with a gradient of CH$_2$Cl$_2$:MeOH—100:0 to 85:15, to give the title compound. MS: m/z=165 (M+1).

Step B. 4,5-Bis(bromomethyl)pyridine-2-carbonitrile

To a solution of 4,5-bis(hydroxymethyl)pyridine-2-carbonitrile from Step A (750 mg, 4.57 mmol) in THF (15 mL) was added phosphorus tribromide (1.61 g, 5.94 mmol) in THF (5 mL) dropwise. The reaction mixture was stirred at ambient temperature for 2 h, and then cooled to 0° C. Saturated aqueous NaHCO$_3$ (5 mL) was added slowly and the quenched mixture was extracted with CHCl$_3$ (2×30 mL). The combined organic extracts were dried over Na$_2$SO$_4$, filtered, and concentrated in vacuo. The crude product was purified by silica gel chromatography, eluting with a gradient of hexane: EtOAc—100:0 to 25:75, to give the title compound. MS: m/z=291 (M+1).

Step C. (±)-2'-Oxo-1',2',5,7-tetrahydrospiro[cyclopenta[c]pyridine-6,3'-pyrrolo[2,3-b]pyridine]-3-carbonitrile To a solution of 4,5-bis(bromomethyl)pyridine-2-carbonitrile from Step B (2.56 g, 8.83 mmol) and 1,3-dihydro-2H-pyrrolo[2,3-b]pyridin-2-one [Marfat & Carta (1987) *Tetrahedron Lett.* 28, 4027] (1.18 g, 8.83 mmol) in THF (120 mL) and H$_2$O (60 mL) was added lithium hydroxide monohydrate (1.11 g, 26.5 mmol). After 20 min, the reaction mixture was poured onto water (100 mL) and extracted with EtOAc (3×100 mL). The combined organic extracts were dried over Na$_2$SO$_4$, filtered, and concentrated in vacuo. The crude product was purified by silica gel chromatography, eluting with a gradient of CH$_2$Cl$_2$:MeOH:NH$_4$OH—100:0:0 to 95:5:1, to give the title compound. MS: m/z=263 (M+1).

Step D. (±)-Sodium 2'-oxo-1',2',5,7-tetrahydrospiro[cyclopenta[c]pyridine-6,3'-pyrrolo[2,3-b]pyridine]-3-carboxylate To a solution of (±)-2'-oxo-1',2',5,7-tetrahydrospiro[cyclopenta[c]pyridine-6,3'-pyrrolo[2,3-b]pyridine]-3-carbonitrile from Step C (1.53 g, 5.83 mmol) in EtOH (20 mL) was added 5 M aqueous NaOH (3.50 mL). The mixture was heated at reflux for 72 h, with additional 5 M aqueous NaOH (2.00 mL) added at 6 h. The reaction mixture was allowed to cool and was concentrated to dryness in vacuo to afford the title compound in sufficient purity for use in subsequent steps. MS: m/z=282 (M+1).

INTERMEDIATE 3

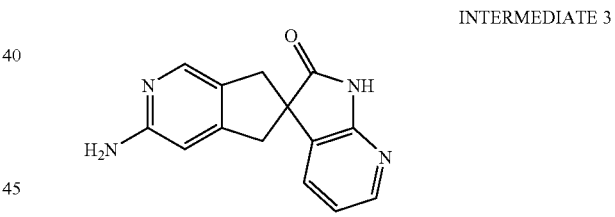

(±)-3-Amino-5,7-dihydrospiro[cyclopenta[c]pyridine-6,3'-pyrrolo[2,3-b]pyridin]-2'(1'H)-one Step A. (±)-tert-Butyl (2'-oxo-1',2',5,7-tetrahydrospiro[cyclopenta[c]pyridine-6,3'-pyrrolo[2,3-b]pyridin]-3-yl)carbamate To a suspension of (±)-sodium 2'-oxo-1',2',5,7-tetrahydrospiro[cyclopenta[c]pyridine-6,3'-pyrrolo[2,3-b]pyridine]-3-carboxylate (1.64 g, 5.83 mmol, described in Intermediate 2) and triethylamine (1.62 mL, 11.7 mmol) in tert-butanol (50 mL) was added diphenylphosphoryl azide (1.89 mL, 8.75 mmol) and the mixture was heated at reflux for 72 h. Additional diphenylphosphoryl azide (1.89 mL, 8.75 mmol) was added after 24 h and 56 h. The reaction mixture was concentrated in vacuo and then partitioned between CH$_2$Cl$_2$ (75 mL) and saturated NaHCO$_3$ (100 mL). The organic layer was separated and the aqueous layer was further extracted with CH$_2$Cl$_2$ (2×50 mL). The combined organic layers were dried over Na$_2$SO$_4$, filtered, and concentrated in vacuo. The crude product was purified by silica gel chromatography, eluting with a gradient of CH$_2$Cl$_2$:MeOH:NH$_4$OH—100:0:0 to 95:5:1, to give the title compound. MS: m/z=353 (M+1).

Step B. (±)-3-Amino-5,7-dihydrospiro[cyclopenta[c] pyridine-6,3'-pyrrolo[2,3-b]pyridin]-2'(1'H)-one trifluoroacetate A solution of (±)-tert-butyl (2'-oxo-1',2',5,7-tetrahydrospiro[cyclopenta[c]pyridine-6,3'-pyrrolo[2,3-b]pyridin]-3-yl)carbamate from Step A (131 mg, 0.372 mmol) was stirred in CH$_2$Cl$_2$ (10 mL) and TFA (3 mL) for 18 h and then concentrated in vacuo to provide the title compound. MS: m/z=253 (M+1).

INTERMEDIATE 4

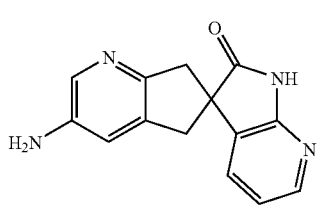

(±)-3-Amino-5,7-dihydrospiro[cyclopenta[b]pyridine-6,3'-pyrrolo[2,3-b]pyridin]-2'(1'H)-one trifluoroacetate Step A. (±)-1'-{[2-(Trimethylsilyl)ethoxy]methyl}-3H-spiro[cyclopentane-1,3'-pyrrolo[2,3-b]pyridine]-2',3(1'H)-dione To a solution of 1-{[2-(trimethylsilyl)ethoxy]methyl}-1,3-dihydro-2H-pyrrolo[2,3-b]pyridin-2-one (2.50 g, 9.46 mmol, described in Intermediate 1) and cesium carbonate (6.78 g, 20.8 mmol) in DMF (45 mL) was added dropwise a solution of 1,4-dibromobutan-2-one (1.59 mL, 12.3 mmol) [de Meijere et al. (2001) *Eur. J. Org. Chem.* 3789] in DMF (45 mL). After 68 h, the mixture was partitioned between Et$_2$O (200 mL) and H$_2$O (200 mL). The organic layer was separated and the aqueous layer was further extracted with Et$_2$O (2×100 mL). The combined organic layers were dried over Na$_2$SO$_4$, filtered, and concentrated in vacuo. The crude product was purified by silica gel chromatography, eluting with a gradient of hexane:EtOAc—100:0 to 75:25, to give the title compound. MS: m/z=333 (M+1).

Step B. (±)-3-Nitro-1'-{[2-(trimethylsilyl)ethoxy] methyl}-5,7-dihydrospiro[cyclopenta[b]pyridine-6, 3'-pyrrolo[2,3-b]pyridin]-2'(1'H)-one A mixture of (±)-1'-{[2-(trimethylsilyl)ethoxy]methyl}-3H-spiro[cyclopentane-1,3'-pyrrolo[2,3-b]pyridine]-2',3 (1'H)-dione from Step A (230 mg, 0.692 mmol) and 1-methyl-3,5-dinitropyridin-2(1H)-one (173 mg, 0.869 mmol) [Tohda et al. (1990) *Bull. Chem. Soc. Japan* 63, 2820] in 2 M ammonia in MeOH (3.5 mL) was heated to reflux for 18 h. The mixture was concentrated in vacuo and purified by silica gel chromatography, eluting with a gradient of hexane: EtOAc—100:0 to 50:50, to give the title compound. MS: m/z=413 (M+1).

Step C. (±)-3-Amino-1'-{[2-(trimethylsilyl)ethoxy] methyl}-5,7-dihydrospiro[cyclopenta[b]pyridine-6, 3'-pyrrolo[2,3-b]pyridin]-2'(1'H)-one A mixture of 10% Pd/C (20 mg) and (±)-3-nitro-1'-{[2-(trimethylsilyl)ethoxy]methyl}-5,7-dihydrospiro[cyclopenta[b]pyridine-6,3'-pyrrolo[2,3-b]pyridin]-2'(1'H)-one from Step B (117 mg, 0.284 mmol) was stirred vigorously in MeOH (5 mL) under an atmosphere of hydrogen (ca. 1 atm). After 4.5 h, the mixture was filtered through a pad of Celite, washing extensively with MeOH, and the filtrate was concentrated in vacuo to give the title compound. MS: m/z=383 (M+1).

Step D. (±)-3-Amino-5,7-dihydrospiro[cyclopenta[b] pyridine-6,3'-pyrrolo[2,3-b]pyridin]-2'(1'H)-one trifluoroacetate A solution of (±)-3-amino-1'-{[2-(trimethylsilyl)ethoxy] methyl}-5,7-dihydrospiro[cyclopenta[b]pyridine-6,3'-pyrrolo[2,3-b]pyridin]-2'(1'H)-one from Step C (117 mg, 0.306 mmol) in MeOH (5 mL) was saturated with HCl (g). The mixture was stirred for 30 min and then concentrated in vacuo. The residue was dissolved in MeOH (3 mL), treated with ethylenediamine (0.020 mL, 0.306 mmol), and 10 N sodium hydroxide was added to adjust the mixture to pH 10. After 1 h, the reaction mixture was purified directly by HPLC using a reversed phase C18 column and eluting with a gradient of H$_2$O:CH$_3$CN:CF$_3$CO$_2$H—90:10:0.1 to 5:95:0.1. MS: m/z=253 (M+1).

INTERMEDIATE 5

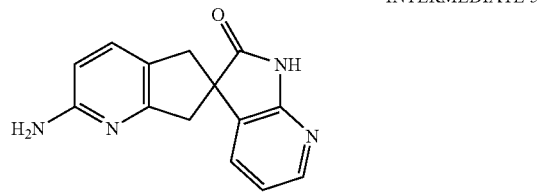

(±)-2-Amino-5,7-dihydrospiro[cyclopenta[b]pyridine-6,3'-pyrrolo[2,3-b]pyridin]-2'(1'H)-one Step A. Dimethyl 6-cyanopyridine-2,3-dicarboxylate To a solution of dimethylpyridine-2,3-dicarboxylate 1-oxide [Niiyami et al. (2002) *Bioorg. Med. Chem. Lett.* 12, 3041] (15.3 g, 72.5 mmol) and trimethylsilyl cyanide (15.7 mL, 117 mmol) in DME (161 mL) was added dimethylcarbamoyl chloride (10.5 mL, 114 mmol). The reaction mixture was heated at reflux for 72 h, and then cooled to 0° C. Saturated aqueous NaHCO$_3$ (800 mL) was added slowly and the quenched mixture was extracted with EtOAc (2×1 L). The combined organic extracts were washed with brine (200 mL), dried over Na$_2$SO$_4$, filtered, and concentrated in vacuo. The crude product was purified by silica gel chromatography, eluting with a gradient of hexane:EtOAc—100:0 to 50:50, to give the title compound. MS: m/z=221 (M+1).

Step B. 5,6-Bis(hydroxymethyl)pyridine-2-carbonitrile

To a solution of dimethyl 6-cyanopyridine-2,3-dicarboxylate from Step A (13.0 g, 59.0 mmol) in EtOH (295 mL) was added lithium borohydride (29.5 mL of a 2 M solution in THF, 59.0 mmol) dropwise. The reaction mixture was stirred at ambient temperature for 4 h, and then cooled to 0° C. Saturated aqueous NaHCO₃ (200 mL) was added slowly and the quenched mixture was extracted with EtOAc (9×100 mL). The combined organic extracts were dried over Na₂SO₄, filtered, and concentrated in vacuo. The crude product was purified by silica gel chromatography, eluting with a gradient of CH₂Cl₂:MeOH—100:0 to 85:15, to give the title compound. MS: m/z=165 (M+1).

Step C. 5,6-Bis(bromomethyl)pyridine-2-carbonitrile

To a solution of 5,6-bis(hydroxymethyl)pyridine-2-carbonitrile from Step B (2.50 g, 15.2 mmol) in THF (76 mL) was added phosphorus tribromide (5.36 g, 19.8 mmol) in THF (20 mL) dropwise. The reaction mixture was stirred at ambient temperature for 2 h, and then cooled to 0° C. Saturated aqueous NaHCO₃ (20 mL) was added slowly and the quenched mixture was extracted with CH₂Cl₂ (2×200 mL). The combined organic extracts were dried over Na₂SO₄, filtered, and concentrated in vacuo. The crude product was purified by silica gel chromatography, eluting with a gradient of hexane:EtOAc—100:0 to 30:70, to give the title compound. MS: m/z=291 (M+1).

Step D. (±)-2'-Oxo-1'-{[2-(trimethylsilyl)ethoxy]methyl}-1',2',5,7-tetrahydrospiro[cyclopenta[b]pyridine-6,3'-pyrrolo[2,3-b]pyridine]-2-carbonitrile To a solution of 5,6-bis(bromomethyl)pyridine-2-carbonitrile from Step C (1.80 g, 6.21 mmol) and 1-{[2-(trimethylsilyl)ethoxy]methyl}-1,3-dihydro-2H-pyrrolo[2,3-b]pyridin-2-one (1.64 g, 6.21 mmol, described in Intermediate 1) in DMF (207 mL) was added cesium carbonate (6.07 g, 18.6 mmol), portionwise, over 5 min. After 18 h, the mixture was partitioned between CH₂Cl₂ (100 mL), saturated aqueous NaHCO₃ (100 mL) and brine (200 mL). The organic layer was removed and the aqueous layer was extracted further with CH₂Cl₂ (2×100 mL). The combined organic extracts were dried over Na₂SO₄, filtered, and concentrated in vacuo. The crude product was purified by silica gel chromatography, eluting with a gradient of hexane:EtOAc—100:0 to 10:90, to give the title compound. MS: m/z=393 (M+1).

Step E. (±)-2'-Oxo-1',2',5,7-tetrahydrospiro[cyclopenta[b]pyridine-6,3'-pyrrolo[2,3-b]pyridine]-2-carboxylic acid To a solution of (±)-2'-oxo-1'-{[2-(trimethylsilyl)ethoxy]methyl}-1',2',5,7-tetrahydrospiro[cyclopenta[b]pyridine-6,3'-pyrrolo[2,3-b]pyridine]-2-carbonitrile from Step D (690 mg, 1.76 mmol) in THF (5 mL) was added 3 N aqueous HCl (36 mL). The mixture was heated at reflux for 18 h, allowed to cool and concentrated to dryness in vacuo. The reaction mixture was dissolved in water (12 mL) and purified directly by HPLC using a reversed phase C18 column and eluting with a gradient of H₂O:CH₃CN:CF₃CO₂H—95:5:0.1 to 5:95:0.1. Lyophilization of the product-containing fractions provided the title compound. MS: m/z=282 (M+1).

Step F. (±)-tert-Butyl (2'-oxo-1',2',5,7-tetrahydrospiro[cyclopenta[b]pyridine-6,3'-pyrrolo[2,3-b]pyridin]-2-yl)carbamate To a suspension of (±)-2'-oxo-1',2',5,7-tetrahydrospiro[cyclopenta[b]pyridine-6,3'-pyrrolo[2,3-b]pyridine]-2-carboxylic acid from Step E (224 mg, 0.796 mmol) and triethylamine (0.333 mL, 2.39 mmol) in tert-butanol (5 mL) was added diphenylphosphoryl azide (0.258 mL, 1.20 mmol) and the mixture was heated at reflux for 1 h. The reaction mixture was concentrated in vacuo and then partitioned between CH₂Cl₂ (20 mL) and saturated NaHCO₃ (20 mL). The organic layer was separated and the aqueous layer was further extracted with CH₂Cl₂ (2×20 mL). The combined organic layers were dried over Na₂SO₄, filtered, and concentrated in vacuo. The crude product was purified by silica gel chromatography, eluting with a gradient of CH₂Cl₂:MeOH:NH₄OH—100:0:0 to 95:5:1, to give the title compound. MS: m/z=353 (M+1).

Step G. (±)-2-Amino-5,7-dihydrospiro[cyclopenta[b]pyridine-6,3'-pyrrolo[2,3-b]pyridin]-2'(1'H)-one A solution of (±)-tert-butyl (2'-oxo-1',2',5,7-tetrahydrospiro[cyclopenta[b]pyridine-6,3'-pyrrolo[2,3-b]pyridin]-2-yl)carbamate from Step F (147 mg, 0.417 mmol) was stirred in CH₂Cl₂ (6 mL) and TFA (1 mL) for 3 h and then concentrated in vacuo to provide the title compound as the TFA salt. MS: m/z=253 (M+1).

INTERMEDIATE 8

N-(2-Oxo-2,3-dihydro-1H-indol-4-yl)glycine

Step A. 4-Nitro-1,3-dihydro-2H-indol-2-one

A mixture of 4-nitroindole (12.2 g, 75.2 mmol) and N-chlorosuccinimide (6.07 g, 30.1 mmol) in CHCl₃ (500 mL) was heated at reflux for 30 h, then concentrated to dryness under reduced pressure. The residue was dissolved in AcOH (200 mL) and the resulting solution was warmed to 70° C., then 85% H₃PO₄ (80 mL) was added over 2 min. The mixture was heated to reflux for 90 min then cooled on ice. The cooled mixture was adjusted to pH 6 by addition of 10 N NaOH (450 mL), followed by aqueous NaHCO₃, keeping the temperature below 30° C. The mixture was extracted with EtOAc (3×1 L) and the combined organic extracts were dried over Na₂SO₄, filtered, and concentrated in vacuo. The crude product was partially purified by silica gel chromatography, eluting with a gradient of hexane:EtOAc—100:0 to 0:100, and then triturated with MeOH to give the title compound. MS: m/z=179 (M+1).

Step B. 4-Amino-1,3-dihydro-2H-indol-2-one

Essentially following the procedures described in Intermediate 4, but using 4-nitro-1,3-dihydro-2H-indol-2-one from Step A in place of 5-nitro-1'-{[2-(trimethylsilyl)ethoxy]methyl}-1,3-dihydrospiro[indene-2,3'-pyrrolo[2,3-b]pyridin]-2'(1'H)-one, the title compound was obtained. MS: m/z=149 (M+1).

Step C. Benzyl N-(2-oxo-2,3-dihydro-1H-indol-4-yl)glycinate

A mixture of 4-amino-1,3-dihydro-2H-indol-2-one (300 mg, 2.03 mmol), benzyl bromoacetate (0.32 mL, 2.03 mmol), cesium carbonate (660 mg, 2.03 mmol), and potassium iodide (336 mg, 2.03 mmol) in DMF (10 mL) was stirred at 50° C. for 4 h. The cooled reaction mixture was quenched with H₂O (10 mL) and extracted with EtOAc (2×15 mL). The combined organic extracts were dried over Na₂SO₄, filtered, and concentrated in vacuo. The crude product was purified by silica gel chromatography, eluting with a gradient of CH₂Cl₂: EtOAc—100:0 to 80:20, to give the title compound. MS: m/z=297 (M+1).

Step D.
N-(2-Oxo-2,3-dihydro-1H-indol-4-yl)glycine

A mixture of 10% Pd/C (100 mg) and benzyl N-(2-oxo-2,3-dihydro-1H-indol-4-yl)glycinate from Step C (320 mg, 1.08 mmol) was stirred vigorously in EtOH (5 mL), EtOAc (5 mL), and AcOH (1 mL) under an atmosphere of hydrogen (ca. 1 atm). After 4 h, the mixture was filtered through a pad of Celite, washing with MeOH, and the filtrate was concentrated to give the title compound. MS: m/z=207 (M+1).

INTERMEDIATE 9

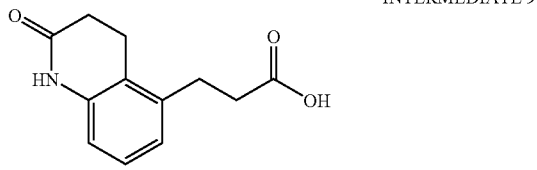

3-(2-Oxo-1,2,3,4-tetrahydroquinolin-5-yl)propanoic acid

Step A. 5-Bromo-3,4-dihydroquinolin-2(1H)-one

To a stirred mixture of sodium azide (862 mg, 13.3 mmol) in H₂O (1.7 mL) and CHCl₃ (6.5 mL) was added conc. H₂SO₄ (0.23 mL, 4.14 mmol). The reaction mixture was stirred vigorously at 0° C. for 2.5 h. The CHCl₃ layer was separated, dried over Na₂SO₄, and added to a solution of 4-bromo-1-indanone (1.12 g, 5.31 mmol) in CHCl₃ (20 mL). To this mixture was added conc. H₂SO₄ (1.75 mL, 31.5 mmol) dropwise over 10 min. The reaction mixture was heated at 45 C for 1 h then poured into ice-water, neutralized with 20% aqueous NaOH, and extracted with CH₂Cl₂ (100 mL). The organic extract was dried over Na₂SO₄, filtered, and concentrated in vacuo. The crude product was purified by silica gel chromatography, eluting with a gradient of CH2Cl2:EtOAc—100:0 to 80:20, to give the title compound. MS: m/z=226 (M+1).

Step B. Ethyl (2E)-3-(2-oxo-1,2,3,4-tetrahydroquinolin-5-yl)acrylate

A mixture of 5-bromo-3,4-dihydroquinolin-2(1H)-one from Step A (50 mg, 0.22 mmol), ethyl acrylate (0.048 mL, 0.44 mmol), triethylamine (0.062 mL, 0.44 mmol), and (PPh₃)₄Pd (26 mg, 0.022 mmol) in DMF (0.5 mL) was heated at 180° C. in a microwave reactor for 4 h. The reaction mixture was partitioned between CH₂Cl₂ (20 mL) and saturated aqueous NaHCO₃ (10 mL). The organic layer was washed with brine, dried over Na₂SO₄, filtered, and concentrated in vacuo. The crude mixture was partially purified by HPLC using a reversed phase C18 column and eluting with a gradient of H₂O:CH₃CN:CF₃CO₂H—90:10:0.1 to 5:95:0.1 to give the title compound in sufficient purity for use in the next step. MS: m/z=246 (M+1).

Step C.
3-(2-Oxo-1,2,3,4-tetrahydroquinolin-5-yl)propanoic acid

A mixture of 10% Pd/C (5 mg) and ethyl (2E)-3-(2-oxo-1,2,3,4-tetrahydroquinolin-5-yl)acrylate from Step B (16 mg, 0.065 mmol) was stirred vigorously in MeOH (2 mL) under an atmosphere of hydrogen (ca. 1 atm). After 4 h, the mixture was filtered through a pad of Celite, washing with MeOH, and the filtrate was concentrated. The residue was dissolved in MeOH (1 mL) and 1 N aqueous NaOH (0.1 mL) and the resulting mixture was stirred at ambient temperature for 18 h. To the reaction mixture was added 1 N aqueous HCl (0.1 mL) and the resulting mixture was concentrated to dryness under reduced pressure to give the title compound. MS: m/z=220 (M+1).

INTERMEDIATE 10

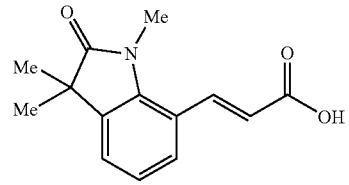

(2E)-3-(1,3,3-Trimethyl-2-oxo-2,3-dihydro-1H-indol-7-yl)acrylic acid

Step A.
7-Bromo-1,3,3-trimethyl-1,3-dihydro-2H-indol-2-one

To a solution of 7-bromo-1,3-dihydro-2H-indol-2-one (200 mg, 0.94 mmol) in DMF (5 mL) were added cesium carbonate (676 mg, 2.07 mmol) and iodomethane (294 mg, 2.07 mmol). The reaction mixture was stirred at ambient temperature for 18 h, then partitioned between H₂O (50 mL) and EtOAc (100 mL). The organic extract was dried over Na₂SO₄, filtered, and concentrated in vacuo. The crude product was purified by silica gel chromatography, eluting with a gradient of hexane:EtOAc—100:0 to 85:15, to give the title compound. MS: m/z=254 (M+1).

Step B. Ethyl (2E)-3-(1,3,3-trimethyl-2-oxo-2,3-dihydro-1H-indol-7-yl)acrylate

A mixture of 7-bromo-1,3,3-trimethyl-1,3-dihydro-2H-indol-2-one from Step A (112 mg, 0.44 mmol), ethyl acrylate (0.238 mL, 2.20 mmol), triethylamine (0.124 mL, 0.88 mmol), and (PPh₃)₄Pd (51 mg, 0.044 mmol) in DMF (1.5 mL) was heated at 180° C. in a microwave reactor for 4 h. The reaction mixture was partitioned between CH₂Cl₂ (50 mL) and saturated aqueous NaHCO₃ (50 mL). The organic layer was washed with brine, dried over Na₂SO₄, filtered, and concentrated in vacuo. The crude mixture was purified by silica gel chromatography, eluting with a gradient of CH₂Cl₂: EtOAc—100:0 to 60:40, to give the title compound. MS: m/z=274 (M+1).

Step C. (2E)-3-(1,3,3-Trimethyl-2-oxo-2,3-dihydro-1H-indol-7-yl)acrylic acid

To a solution of ethyl (2E)-3-(1,3,3-trimethyl-2-oxo-2,3-dihydro-1H-indol-7-yl)acrylate (25 mg, 0.091 mmol) in MeOH (1 mL) was added 1 N aqueous NaOH (0.1 mL) and the resulting mixture was stirred at ambient temperature for 18 h. To the reaction mixture was added 1 N aqueous HCl (0.1 mL) and the resulting mixture was concentrated to dryness under reduced pressure to give the title compound. MS: m/z=246 (M+1).

EXAMPLE 1

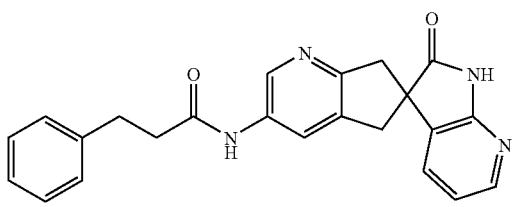

N-(2'-Oxo-1',2',5,7-tetrahydrospiro[cyclopenta[b]pyridine-6,3'-pyrrolo[2,3-b]pyridin]-3-yl)-3-phenyl-propanamide A mixture of 3-phenylpropionic acid (35 mg, 0.23 mmol), (±)-3-amino-5,7-dihydrospiro[cyclopenta[b]pyridine-6,3'-pyrrolo[2,3-b]pyridin]-2'(1'H)-one (71 mg, 0.28 mmol, described in Intermediate 4), N,N,N',N'-bis(tetramethylene)chloroformamidinium hexafluorophosphate (153 mg, 0.46 mmol), and N,N-diisopropylethylamine (0.20 mL, 1.15 mmol) in THF (2 mL) is stirred at ambient temperature for 18 h. The reaction mixture is purified directly by HPLC using a reversed phase C18 column and eluting with a gradient of $H_2O:CH_3CN:CF_3CO_2H$—90:10:0.1 to 5:95:0.1. The pure, product-containing fractions are combined and made basic with saturated aqueous $NaHCO_3$. The resulting mixture is extracted with EtOAc (3×20 mL), and the combined organic extracts are washed with brine, dried over $Na_2SO_4$, filtered, and concentrated in vacuo to provide the title compound.

EXAMPLES 2-7

Essentially following the procedures outlined for Example 1, the compounds listed in Table 1 are prepared. The requisite carboxylic acids are commercially available, described in the literature, or readily synthesized by one skilled in the art of organic synthesis. In some cases, straightforward protecting group strategies are applied.

TABLE 1

| Example | $R^b$ |
|---|---|
| 2 | phenylcyclopropyl-CHO |

TABLE 1-continued

| Example | $R^b$ |
|---|---|
| 3 | 3,5-dibromobenzaldehyde |
| 4 | bicyclic norbornane acetaldehyde |
| 5 | 3-cyclohexylpropanal |
| 6 | indane-2-carbaldehyde |
| 7 | 3-phenoxypropanal |

EXAMPLES 8-13

Essentially following the procedures outlined for Example 1, but using Intermediate 3 in place of Intermediate 4, the compounds listed in Table 2 are prepared. The requisite carboxylic acids are commercially available, described in the literature, or readily synthesized by one skilled in the art of organic synthesis. In some cases, straightforward protecting group strategies are applied.

TABLE 2

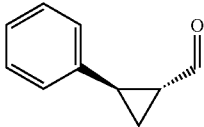

| Example | $R^b$ |
|---------|-------|
| 8 | 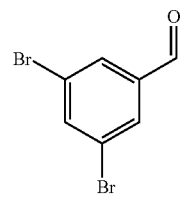 |
| 9 | 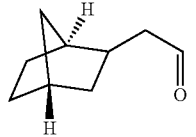 |
| 10 | 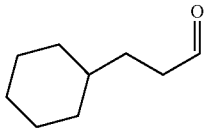 |
| 11 | 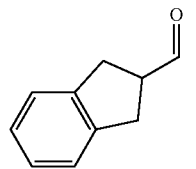 |
| 12 | 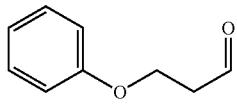 |
| 13 | 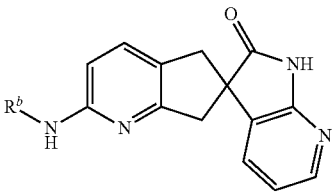 |

EXAMPLES 14-19

Essentially following the procedures outlined for Example 1, but using Intermediate 5 in place of Intermediate 4, the compounds listed in Table 3 are prepared. The requisite carboxylic acids are commercially available, described in the literature, or readily synthesized by one skilled in the art of organic synthesis. In some cases, straightforward protecting group strategies are applied.

TABLE 3

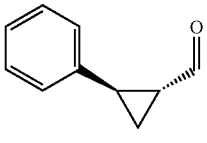

| Example | $R^b$ |
|---------|-------|
| 14 | 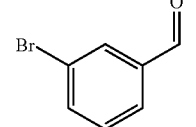 |
| 15 | 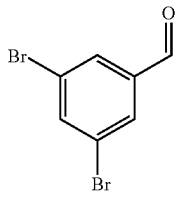 |
| 16 | 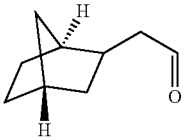 |
| 17 | 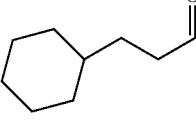 |
| 18 | 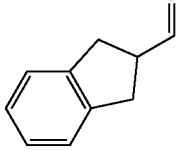 |
| 19 | 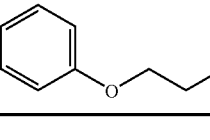 |

Although specific enantiomers and diastereomers appear in the above Examples and Intermediates, it is well understood by those skilled in the art that modifications to reaction conditions and reagents (for example, but not limited to: using the opposite chirality for starting materials; different catalysts; using the opposite chirality for reagents; choosing to use a different enantiomer or diasteriomer subsequent to a chiral resolution) will provide alternative enantiomers and diastereomers, all of which are included in the spirit and scope of the invention. It is intended that all of the possible optical isomers and diastereomers in mixtures and as pure or partially purified compounds are included within the ambit of this invention. The present invention is meant to comprehend all such isomeric forms of these compounds.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

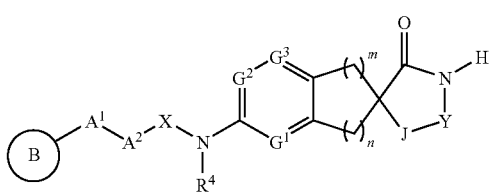

wherein:

B is a selected from the group consisting of: $C_{3-10}$cycloalkyl, phenyl, naphthyl, tetrahydronaphthyl, indanyl, biphenyl, phenanthryl, anthryl, azepanyl, azepinyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepanyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiazolyl, thiazolinyl, thienofuryl, thienothienyl, thienyl and triazolyl, where B is linked to $A^1$ via a carbon atom in B, and where B is unsubstituted or substituted with 1-5 substituents, each substituent independently selected from $R^1$, $R^2$, $R^{3a}$ and $R^{3b}$, wherein $R^1$, $R^2$, $R^{3a}$ and $R^{3b}$ are each independently selected from:
(1) —$C_{1-6}$alkyl, which is unsubstituted or substituted with 1-7 substituents, each substituent independently selected from:
(a) halo,
(b) hydroxy,
(c) —O—$C_{1-6}$alkyl,
(d) —$C_{3-6}$cycloalkyl,
(e) phenyl or heterocycle, wherein heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each substituent independently selected from: —$C_{1-6}$alkyl, —O—$C_{1-6}$alkyl, halo, hydroxy, trifluoromethyl and —$OCF_3$,
(f) —$CO_2R^9$, wherein $R^9$ is selected from: hydrogen, —$C_{5-6}$ cycloalkyl, benzyl, phenyl, and —$C_{1-6}$alkyl which is unsubstituted or substituted with 1-6 fluoro,
(g) —$NR^{10}R^{11}$, wherein $R^{10}$ and $R^{11}$ are each independently selected from: hydrogen, —$C_{5-6}$ cycloalkyl, benzyl, phenyl, —$COR^9$, —$SO_2R^{12}$, and —$C_{1-6}$alkyl which is unsubstituted or substituted with 1-6 fluoro,
(h) —$SO_2R^{12}$, wherein $R^{12}$ is selected from: —$C_{5-6}$ cycloalkyl, benzyl, phenyl and —$C_{1-6}$alkyl which is unsubstituted or substituted with 1-6 fluoro,
(i) —$CONR^{10a}R^{11a}$ wherein $R^{10a}$ and $R^{11a}$ are each independently selected from: hydrogen, —$C_{5-6}$ cycloalkyl, benzyl, phenyl and —$C_{1-6}$alkyl which is unsubstituted or substituted with 1-6 fluoro,
or wherein $R^{10a}$ and $R^{11a}$ join to form a ring selected from azetidinyl, pyrrolidinyl, piperidinyl, piperazinyl, and morpholinyl, where said ring is unsubstituted or substituted with 1-5 substituents, each substituent independently selected from: —$C_{1-6}$alkyl, —O—$C_{1-6}$alkyl, halo, hydroxyl, phenyl and benzyl,
(j) trifluoromethyl,
(k) —$OCO_2R^9$,
(l) —$(NR^{10a})CO_2R^9$,
(m) —$O(CO)NR^{10a}R^{11a}$, and
(n) —$(NR^9)(CO)NR^{10a}R^{11a}$,
(2) —$C_{3-6}$cycloalkyl, which is unsubstituted or substituted with 1-7 substituents each independently selected from:
(a) halo,
(b) hydroxy,
(c) —O—$C_{1-6}$alkyl,
(d) trifluoromethyl, and
(e) phenyl, which is unsubstituted or substituted with 1-5 substituents each independently selected from: —$C_{1-6}$alkyl, —O—$C_{1-6}$alkyl, halo, hydroxy and trifluoromethyl,
(3) phenyl or heterocycle, wherein heterocycle is selected from: pyridyl, pyrimidinyl, pyrazinyl, thienyl, pyridazinyl, pyrrolidinyl, azetidinyl, thiazolyl, isothiazolyl, oxazolyl, isoxazolyl, imidazolyl, triazolyl, tetrazolyl, azepanyl, azepinyl, benzimidazolyl, benzopyranyl, benzofuryl, benzothiazolyl, benzoxazolyl, chromanyl, furyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, quinazolinyl, 1,3-dioxolanyl, oxadiazolyl, piperidinyl and morpholinyl, where said phenyl or heterocycle is unsubstituted or substituted with 1-5 substituents each independently selected from:
(a) —$C_{1-6}$alkyl which is unsubstituted or substituted with 1-6 fluoro,
(b) halo,
(c) hydroxy, (d) —O—$C_{1-6}$alkyl which is unsubstituted or substituted with 1-6 fluoro,
(e) —$C_{3-6}$cycloalkyl,
(f) phenyl or heterocycle, wherein heterocycle is selected from: pyridyl, pyrimidinyl, pyrazinyl, thienyl and morpholinyl, where said phenyl or heterocycle is unsubstituted or substituted with 1-5 substituents each independently selected from: —$C_{1-6}$alkyl, —O—$C_{1-6}$alkyl, halo, hydroxy and trifluoromethyl,
(g) —$CO_2R^9$,
(h) —$NR^{10}R^{11}$,
(i) —$CONR^{10}R^{11}$, and
(j) —$SO_2R^{12}$,
(4) halo,
(5) oxo,
(6) hydroxy,
(7) —O—$C_{1-6}$alkyl which is unsubstituted or substituted with 1-5 halo,
(8) —CN,
(9) —$CO_2R^9$,
(10) —$NR^{10}R^{11}$,
(11) —$SO_2R^{12}$,
(12) —$CONR^{10a}R^{11a}$,
(13) —$OCO_2R^9$,
(14) —$(NR^{10a})CO_2R^9$,
(15) —$O(CO)NR^{10a}R^{11a}$,
(16) —$(NR^9)(CO)NR^{10a}R^{11a}$,
(17) —$SO_2NR^{10a}R^{11a}$, and
(18) —$COR^{12}$;
or $R^{3a}$ and $R^{3b}$ and the atom(s) to which they are attached are join to form a ring selected from cyclobutyl, cyclopentyl, cyclohexyl, cyclopentenyl, cyclohexenyl, azetidinyl, pyrrolidinyl, piperidinyl, tetrahydrofuranyl, tetrahydropyranyl, furanyl, dihydrofuranyl, dihydropyranyl and piperazinyl, where said ring is unsubstituted or substituted with 1-5 substituents each independently selected from:
(a) —$C_{1-6}$alkyl, which is unsubstituted or substituted with 1-3 substituents each independently selected from:
(i) halo,
(ii) hydroxy,
(iii) —O—$C_{1-6}$alkyl,
(iv) —$C_{3-6}$cycloalkyl,
(v) phenyl or heterocycle, wherein heterocycle is selected from: pyridyl, pyrimidinyl, pyrazinyl, pyridazinyl, piperidinyl, piperazinyl, pyrrolidinyl, thienyl, and morpholinyl, where said phenyl or heterocycle is unsubstituted or substituted with 1-5 substituents each independently selected from: —$C_{1-6}$alkyl, —O—$C_{1-6}$alkyl, halo, hydroxy, trifluoromethyl and —$OCF_3$,
(vi) —$CO_2R^9$,
(vii) —$NR^{10}R^{11}$,
(viii) —$SO_2R^{12}$,
(ix) —$CONR^{10a}R^{11a}$, and
(x) —$(NR^{10a})CO_2R^9$,
(b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, where said phenyl or heterocycle is unsubstituted or substituted with 1-3 substituents each independently selected from: halo, hydroxy, —$C_{3-6}$cycloalkyl, —$C_{1-6}$alkyl which is unsubstituted or substituted with 1-6 fluoro and —O—$C_{1-6}$alkyl which is unsubstituted or substituted with 1-6 fluoro,
(c) halo,
(d) —$SO_2R^{12}$,
(e) hydroxy,
(f) —O—$C_{1-6}$alkyl which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$, and
(n) —$(NR^9)(CO)NR^{10a}R^{11a}$;
$A^1$ and $A^2$ are each independently selected from:
(1) a bond,
(2) —$CR^{13}R^{14}$—, wherein $R^{13}$ and $R^{14}$ are independently selected from: hydrogen, hydroxyl and $C_{1-6}$ alkyl which is unsubstituted or substituted with 1-6 fluoro,
(3) —$NR^{10}$—,
(4) —$CR^{13}R^{14}$—$NR^{10}$—,
(5) —$CR^{13}R^{14}$—$CH_2$—,
(6) —$CH_2$—$CR^{13}R^{14}$—,
(7) —O—$CR^{13}R^{14}$—,
(8) —$CR^{13}R^{14}$—O—, and
(9) —C≡C—,
(10) —$C(R^{13})$=$C(R^{14})$—, and
(11) —C(=O)—,
or wherein one of $A^1$ and $A^2$ is absent;
$G^1$, $G^2$ and $G^3$ are each independently selected from:
(1) —$C(R^5)$=,
(2) —N=, and
(3) —$(N^+\text{—}O^-)$=,
wherein no more than two of $G^1$, $G^2$ and $G^3$ are selected to be —$C(R^5)$=;
or wherein $G^1$ is selected from:
(1) —$C(R^5)$=,
(2) —N=, and
(3) —$(N^+\text{—}O^-)$=,
and -$G^2$=$G^3$- taken together are selected from:
(1) —S—,
(2) —O—,
(3) —$N(R^{10})$—;
J is selected from:
(1) =$C(R^{6a})$—,
(2) —$CR^{13}R^{14}$—,
(3) —C(=O)—, and
(4) —$N(R^{15})$—;
Y is selected from:
(1) =$C(R^{6b})$—,
(2) —$CR^{13}R^{14}$—,
(3) —C(=O)—,
(4) —$SO_2$—,
(5) =N—, and
(6) —$N(R^{6b})$—;
X is —CO— or —$SO_2$—;
$R^4$ is selected from: hydrogen, $C_{5-6}$ cycloalkyl, benzyl, phenyl and $C_{1-6}$ alkyl which is unsubstituted or substituted with 1-6 fluoro;
$R^5$ is selected from: hydrogen, $C_{1-6}$ alkyl, —O—$C_{1-6}$alkyl, —$OCF_3$, trifluoromethyl, halo, hydroxy and —CN;
$R^{6a}$ and $R^{6b}$ are each independently selected from:
(1) hydrogen;
(2) —$C_{1-4}$alkyl, which is unsubstituted or substituted with 1-5 substituents independently selected from:

(a) halo,
(b) —O—$C_{1-6}$alkyl,
(c) —$C_{3-6}$cycloalkyl,
(d) phenyl or heterocycle, wherein heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, and morpholinyl, and wherein said phenyl or heterocycle is unsubstituted or substituted with 1-3 substituents independently selected from: —$C_{1-6}$alkyl, —O—$C_{1-6}$alkyl, halo, hydroxy, trifluoromethyl and —$OCF_3$,
(3) phenyl or heterocycle, wherein heterocycle is selected from: pyridyl, pyrimidinyl, pyrazinyl, thienyl, pyrrolidinyl, azetidinyl, thiazolyl, oxazolyl, imidazolyl, triazolyl, tetrahydrofuryl, piperidinyl, and morpholinyl, which is unsubstituted or substituted with 1-3 substituents independently selected from:
  (a) —$C_{1-4}$alkyl, which is unsubstituted or substituted with 1-5 fluoro,
  (b) halo,
  (c) hydroxy,
  (d) —O—$C_{1-4}$alkyl, which is unsubstituted or substituted with 1-5 fluoro,
  (e) —$C_{3-6}$cycloalkyl, and
  (f) phenyl,
(4) halo,
(5) hydroxy,
(6) —O—$C_{1-6}$alkyl, which is unsubstituted or substituted with 1-5 halo,
(7) —CN,
(8) —$CO_2R^9$,
(9) —$NR^{10}R^{11}$, and
(10) —$CONR^{10a}R^{11a}$;
or $R^{6a}$ and $R^{6b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl, and dihydrothiopyranyl, where said ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) hydroxy,
    (iii) —O—$C_{1-6}$alkyl,
    (iv) —$C_{3-6}$cycloalkyl,
    (v) phenyl or heterocycle, wherein heterocycle is selected from: pyridyl, pyrimidinyl, pyrazinyl, pyridazinyl, piperidinyl, piperazinyl, pyrrolidinyl, thienyl, and morpholinyl, which is unsubstituted or substituted with 1-5 substituents each independently selected from: —$C_{1-6}$alkyl, —O—$C_{1-6}$alkyl, halo, hydroxy, trifluoromethyl, and —$OCF_3$,
    (vi) —$CO_2R^9$,
    (vii) —$NR^{10}R^{11}$,
    (viii) —$SO_2R^{12}$,
    (ix) —$CONR^{10a}R^{11a}$, and
    (x) —$(NR^{10a})CO_2R^9$,
  (b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, where said phenyl or heterocycle is unsubstituted or substituted with 1-3 substituents each independently selected from: —$C_{3-6}$cycloalkyl, halo, hydroxy, —O—$C_{1-6}$alkyl which is unsubstituted or substituted with 1-6 fluoro, and —$C_{1-6}$alkyl which is unsubstituted or substituted with 1-6 fluoro,
  (c) halo,
  (d) —$SO_2R^{12}$,
  (e) hydroxy,
  (f) —O—$C_{1-6}$alkyl which is unsubstituted or substituted with 1-5 halo,
  (g) —CN,
  (h) —$COR^{12}$,
  (i) —$NR^{10}R^{11}$,
  (j) —$CONR^{10a}R^{11a}$,
  (k) —$CO_2R^9$,
  (l) —$(NR^{10a})CO_2R^9$,
  (m) —$O(CO)NR^{10a}R^{11a}$,
  (n) —$(NR^9)(CO)NR^{10a}R^{11a}$, and
  (o) oxo;
$R^{15}$ is selected from:
(1) hydrogen,
(2) —$C_{1-6}$alkyl or —$C_{3-6}$cycloalkyl which are unsubstituted or substituted with 1-7 substituents where the substituents are independently selected from:
  (a) halo,
  (b) hydroxy,
  (c) —O—$C_{1-6}$alkyl,
  (d) —$C_{3-6}$cycloalkyl,
  (e) phenyl, which is unsubstituted or substituted with 1-5 substituents where the substituents are independently selected from:
    (i) —$C_{1-6}$alkyl,
    (ii) —O—$C_{1-6}$alkyl,
    (iii) halo,
    (iv) hydroxy, and
    (v) trifluoromethyl,
  (f) —$CO_2R^9$,
  (g) —$NR^{10}R^{11}$,
  (h) —$CONR^{10}R^{11}$,
  (i) —$SO_2R^{12}$, and
  (j) trifluoromethyl, and
(3) phenyl or heterocycle, wherein heterocycle is selected from: pyridyl, pyrimidinyl, pyrazinyl, thienyl, and morpholinyl, which is unsubstituted or substituted with 1-5 substituents where the substituents are independently selected from:
  (a) —$C_{1-6}$alkyl,
  (b) —O—$C_{1-6}$alkyl,
  (c) halo,
  (d) hydroxy, and
  (e) trifluoromethyl;
m is 1 or 2;
n is 1 or 2;
or a pharmaceutically acceptable salt thereof and individual enantiomers and diastereomers thereof.

2. The compound of claim 1 having the formula Ia:

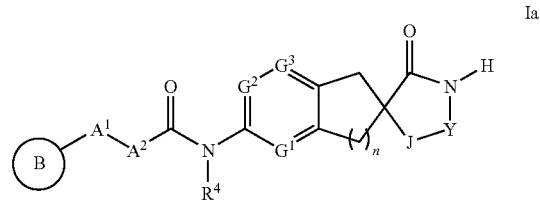

or a pharmaceutically acceptable salt thereof and individual enantiomers and diastereomers thereof.

3. The compound of claim 1 having the formula Ib:

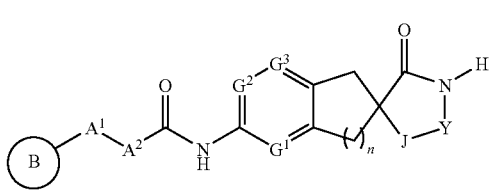

or a pharmaceutically acceptable salt thereof and individual enantiomers and diastereomers thereof.

4. The compound of claim 1 having the formula If:

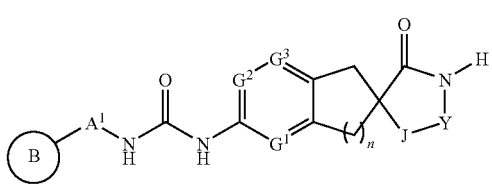

or a pharmaceutically acceptable salt thereof and individual enantiomers and diastereomers thereof.

5. The compound of claim 1 having the formula Ig:

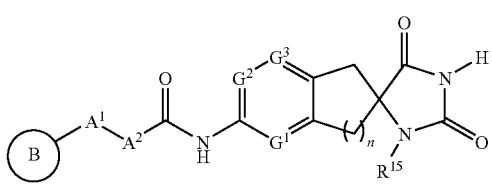

or a pharmaceutically acceptable salt thereof and individual enantiomers and diastereomers thereof.

6. The compound of claim 1 having the formula Ih:

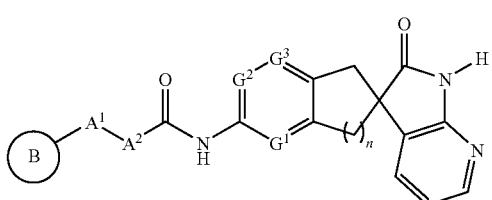

or a pharmaceutically acceptable salt thereof and individual enantiomers and diastereomers thereof.

7. The compound of claim 1, wherein B is selected from: $C_{3-10}$cycloalkyl, phenyl, napthyl, tetrahydronaphthyl, indanyl, indolyl, indolinyl, isoindolinyl, isoquinolinyl, morpholinyl, naphthyridinyl, piperidyl, piperazinyl, pyrazinyl, pyridazinyl, pyridinyl, pyridyl, pyrimidinyl, pyrimidyl, pyrrolidinyl, quinazolinyl, quinolinyl, quinoxalinyl, thiazolyl and thienyl, unsubstituted or substituted with 1-5 substituents each independently selected from $R^1$, $R^2$, $R^{3a}$ and $R^{3b}$, or a pharmaceutically acceptable salt thereof and individual enantiomers and diastereomers thereof.

8. The compound of claim 1, wherein B is phenyl, bicycloheptyl, cyclohexyl or indanyl, or a pharmaceutically acceptable salt thereof and individual enantiomers and diastereomers thereof.

9. The compound of claim 1, wherein $A^1$ is selected from a bond, —$CH_2$—, —$OCH_2$—, —C≡C—, —$CH_2$—$NR^{10}$—, —$NR^{10}$—, and —C(H)=C(H)—, or a pharmaceutically acceptable salt thereof and individual enantiomers and diastereomers thereof.

10. The compound of claim 1, wherein $A^2$ is selected from a bond, —$CH_2$—, —NH— and —$CH_2$—NH—, or a pharmaceutically acceptable salt thereof and individual enantiomers and diastereomers thereof.

11. The compound of claim 1, wherein J is selected from: =C($R^{6a}$)—; —$CH_2$—; and —N($R^{15}$)—, or a pharmaceutically acceptable salt thereof and individual enamtiomers and diastereomers thereof.

12. The compound of claim 1, wherein Y is selected from: =C($R^{6b}$)—; —$CH_2$—; and —C(=O)—, or a pharmaceutically acceptable salt thereof and individual enantiomers and diastereomers thereof.

13. The compound of claim 1, wherein X is —CO— or —$SO_2$—, or a pharmaceutically acceptable salt thereof and individual enantiomers and diastereomers thereof.

14. The compound of claim 1, wherein $R^{6a}$ and $R^{6b}$ are each independently selected from:

(1) hydrogen;

(2) —$C_{1-4}$alkyl, which is unsubstituted or substituted with 1-3 substituents each independently selected from: halo, —O—$C_{1-6}$alkyl, —$C_{3-6}$cycloalkyl and phenyl, (3) phenyl or heterocycle, wherein heterocycle is selected from: pyridyl, pyrimidinyl, pyrazinyl, thiazolyl, oxazolyl, tetrahydrofuryl, piperidinyl, and morpholinyl, where said phenyl or heterocycle is unsubstituted or substituted with 1-3 substituents each independently selected from:

(a) —$C_{1-4}$alkyl, which is unsubstituted or substituted with 1-3 fluoro, (b) halo, (c) hydroxy, and (d) —O—$C_{1-4}$alkyl, which is unsubstituted or substituted with 1-3 fluoro, (4) halo, (5) —$NR^{10}R^{11}$, (6) hydroxy, (7) —O—$C_{1-4}$alkyl, which is unsubstituted or substituted with 1-3 halo, or a pharmaceutically acceptable salt thereof and individual enantiomers and diastereomers thereof.

15. The compound of claim 1, wherein $G^1$ is selected from: —C($R^5$)= and —N=; and -$G^2$=$G^3$- taken together are selected from: —S— and —N($R^{10}$)—, or a pharmaceutically acceptble salt thereof and individual enantiomers and diastereomers thereof.

16. The compound of claim 1, wherein one of $G^1$, $G^2$ and $G^3$ is —N= and the remaining two of $G^1$, $G^2$ and $G^3$ are —C(H)=, or a pharmaceutically acceptable salt thereof and individual enantiomers and diastereomers thereof.

17. A compound selected from:

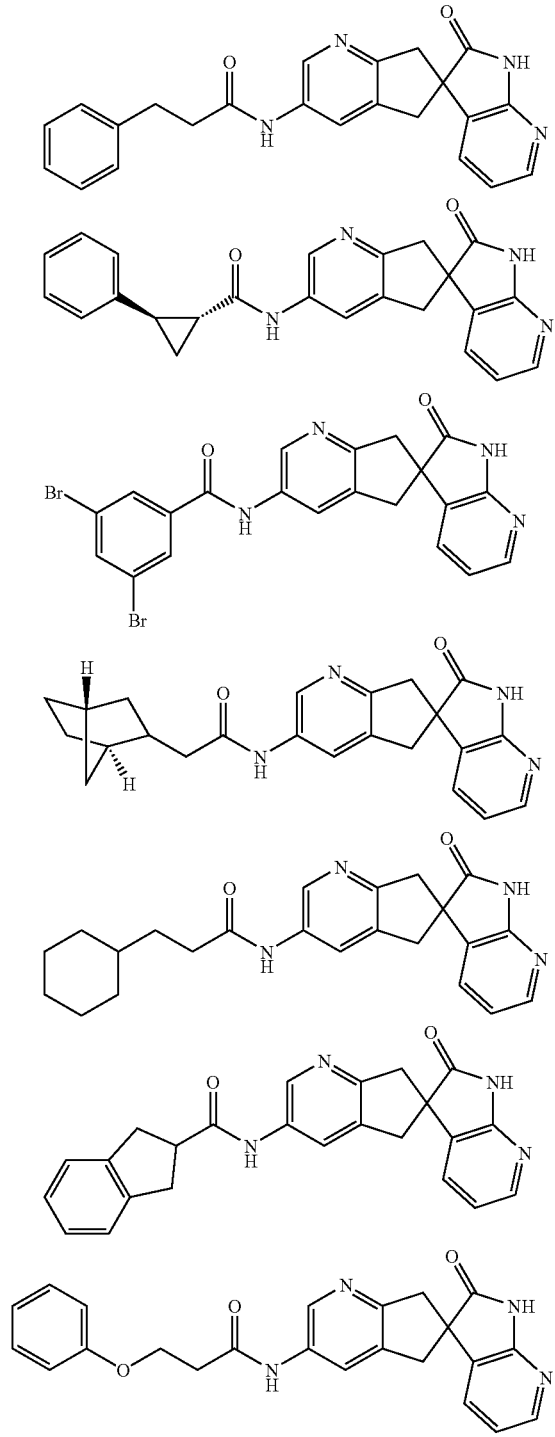

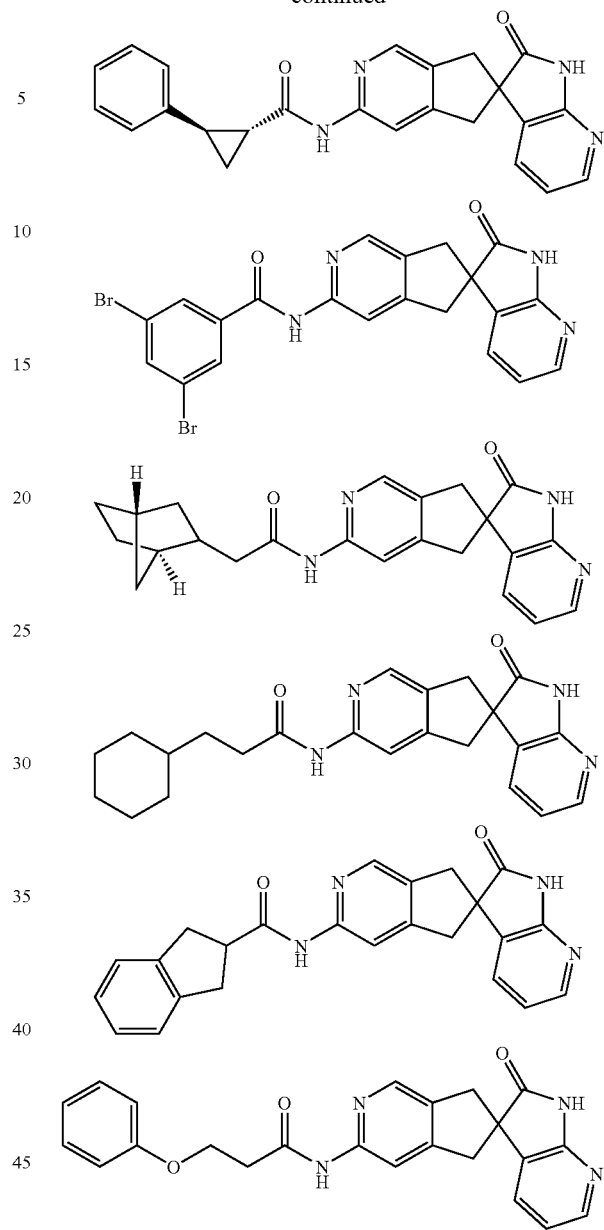

or a pharmaceutically acceptable salt thereof and individual enantiomers and diastereomers thereof.

18. A pharmaceutical composition which comprises an inert carrier and the compound of claim 1.

19. A method for treating headache in a mammalian patient in need of such which comprises administering to the patient a therapeutically effective amount of the compound of claim 1.

* * * * *